(12) United States Patent
Batten et al.

(10) Patent No.: US 6,824,516 B2
(45) Date of Patent: Nov. 30, 2004

(54) SYSTEM FOR EXAMINING, MAPPING, DIAGNOSING, AND TREATING DISEASES OF THE PROSTATE

(75) Inventors: Bobby G. Batten, Williamsburg, VA (US); John A. Companion, Hampton, VA (US)

(73) Assignee: MedSci Technologies, Inc., Newport News, VA (US)

( * ) Notice: Subject to any disclaimer, the term of this patent is extended or adjusted under 35 U.S.C. 154(b) by 103 days.

(21) Appl. No.: 10/385,577

(22) Filed: Mar. 11, 2003

(65) Prior Publication Data

US 2003/0171678 A1 Sep. 11, 2003

Related U.S. Application Data

(60) Provisional application No. 60/362,992, filed on Mar. 11, 2002.

(51) Int. Cl.[7] .................................................. A61B 8/00
(52) U.S. Cl. ...................................... 600/439; 600/459
(58) Field of Search ......................... 600/407, 437–472, 600/587; 606/108; 324/318, 322; 601/2, 3; 128/898; 73/625–633

(56) References Cited

U.S. PATENT DOCUMENTS

| | | | |
|---|---|---|---|
| 5,178,147 A | 1/1993 | Ophir | 128/660.01 |
| 5,282,472 A | 2/1994 | Companion | 128/662.06 |
| 5,398,690 A | 3/1995 | Batten | 128/662.05 |
| 5,810,731 A | 9/1998 | Sarvazyan | 600/438 |
| 5,919,139 A | 7/1999 | Lin | 600/443 |
| 5,952,828 A | 9/1999 | Rossman | 324/318 |
| 6,165,128 A | 12/2000 | Cespedes | 600/463 |

*Primary Examiner*—Ali Imam
(74) *Attorney, Agent, or Firm*—George F. Helfrich

(57) ABSTRACT

A holistically integrated ultrasonic system for examining, mapping, diagnosing, and treating diseases of the prostate gland in a male human includes an ultrasonic transrectal probe and an ultrasonic transurethral probe. Each of these probes is adapted to pulse and to receive, as well as to produce and operate within a liquid-filled volume of the lumen into which they are inserted. Each probe is in operative communication with an integrated patient support platform and an integrated expert system. The integrated expert system collects data transmitted by sensors in the transrectal and transurethral probes and produces level-of-suspicion mapping of the prostate gland with cancer probability assessments for areas contained within the level-of-suspicion mapping. The integrated expert system communicates with, and provides targeting coordinates for operation of an automated slave biopsy subsystem and directs a biopsy needle to a selected point within the prostate gland. The biopsy needle includes a means for extracting a biopsy tissue sample from the prostate gland. The integrated patient support platform includes a multi-degree of freedom positioning chair which optimizes positioning of a patient for scanning and biopsy procedures and affords repeatability thereof.

22 Claims, 34 Drawing Sheets

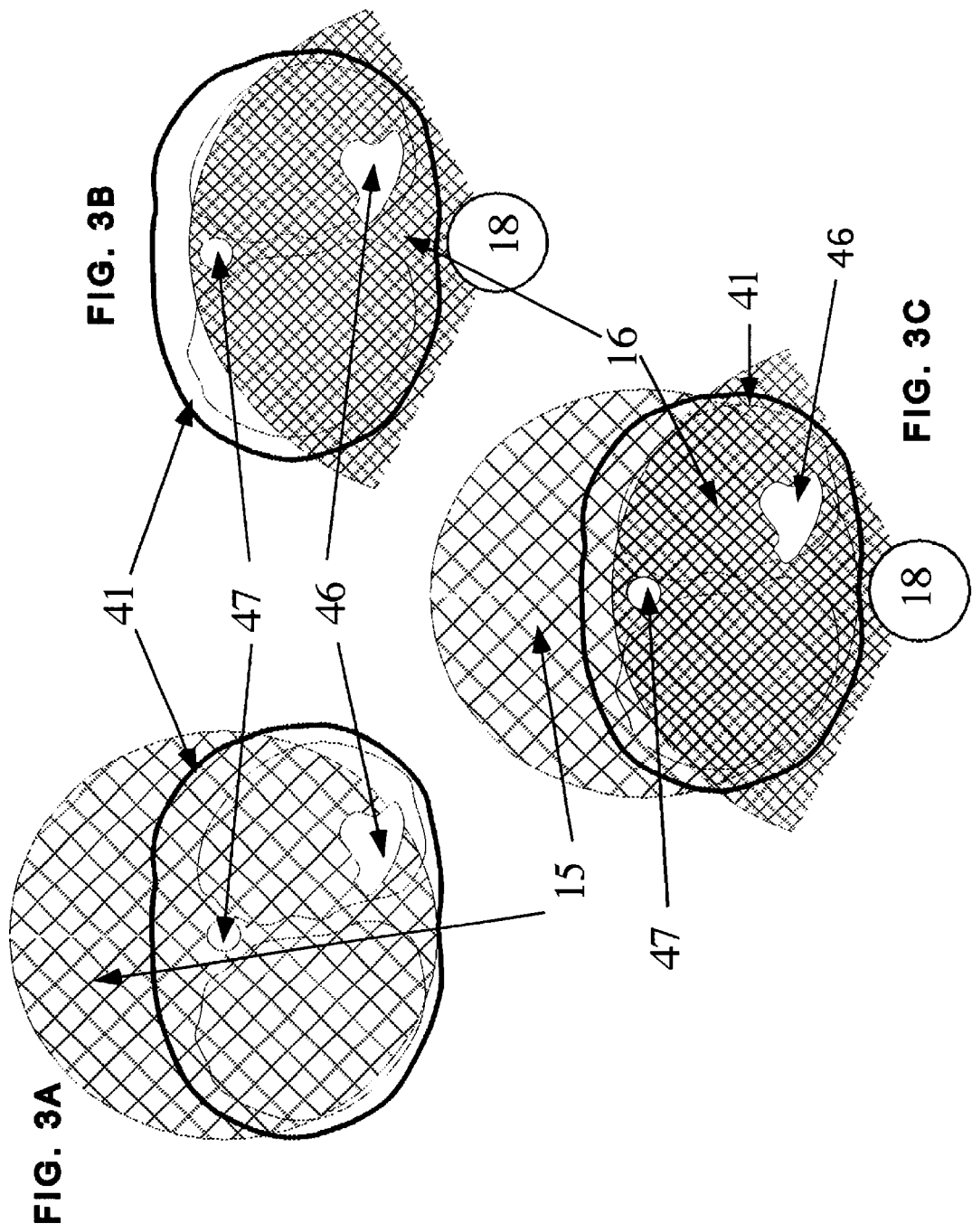

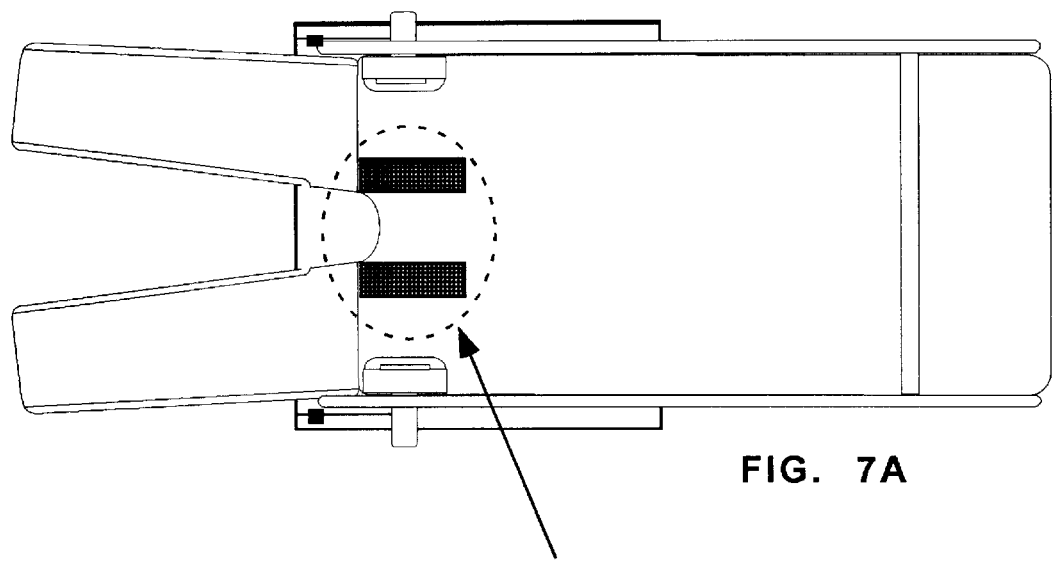
FIG. 7A
FIG. 7B
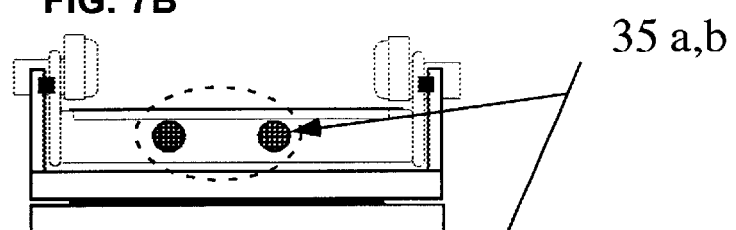
35 a,b
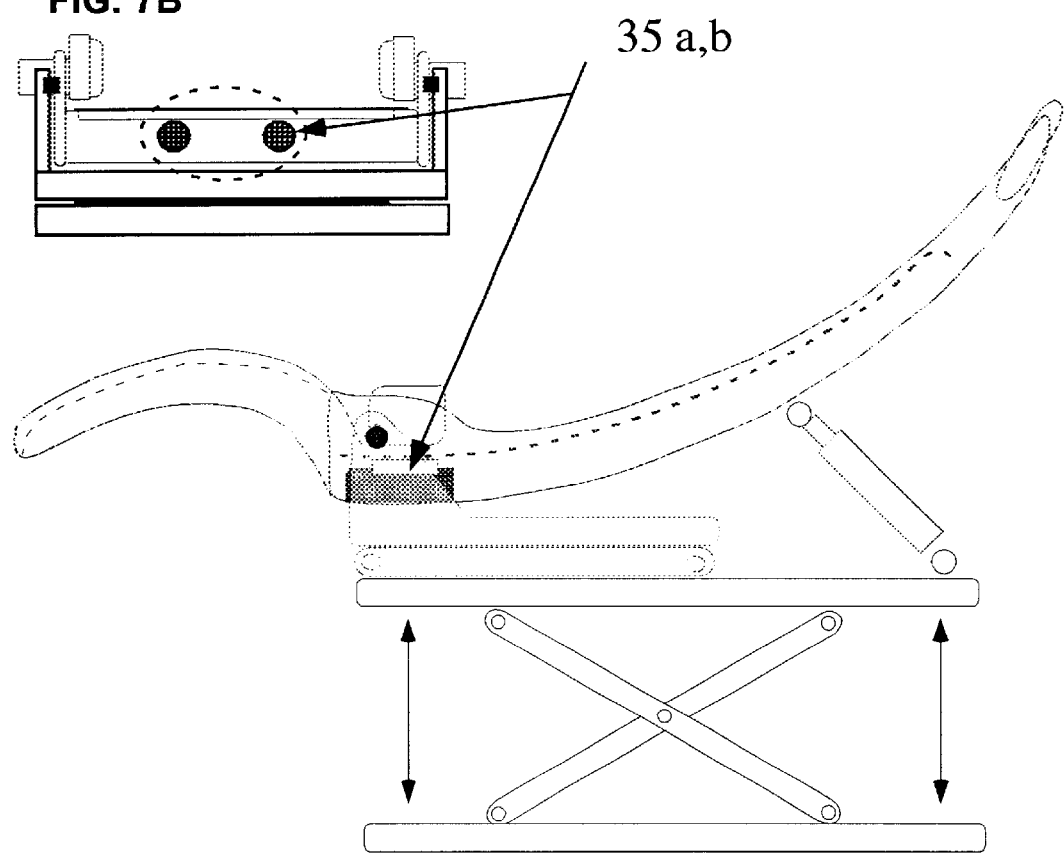
FIG. 7C

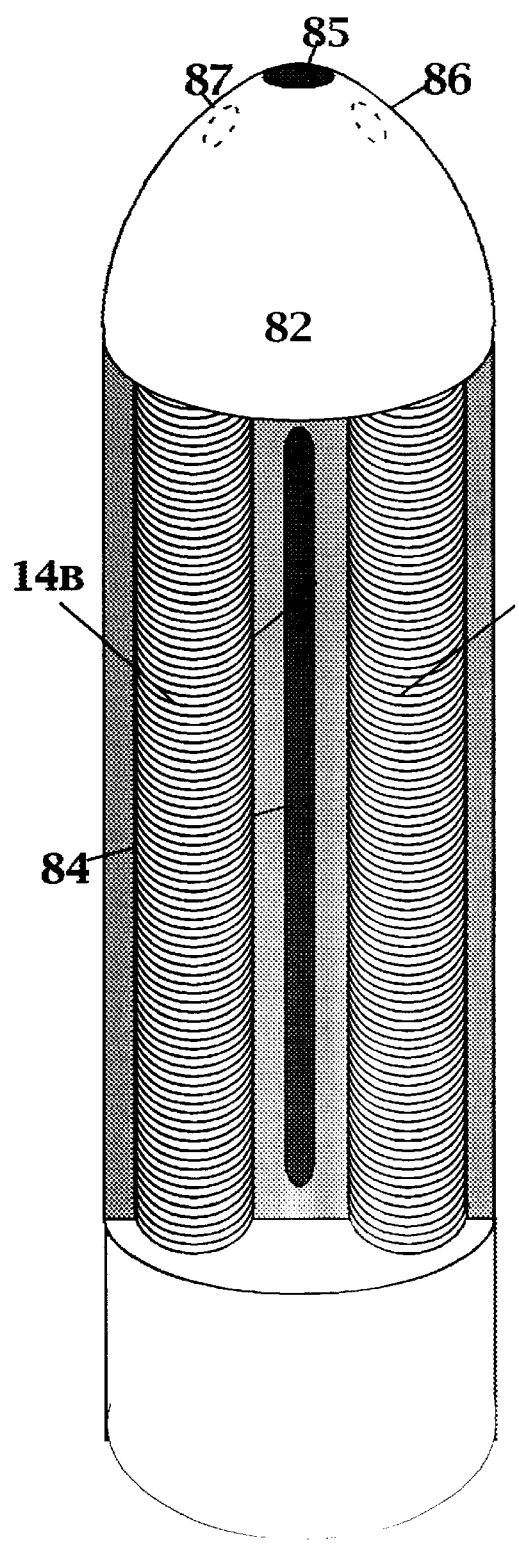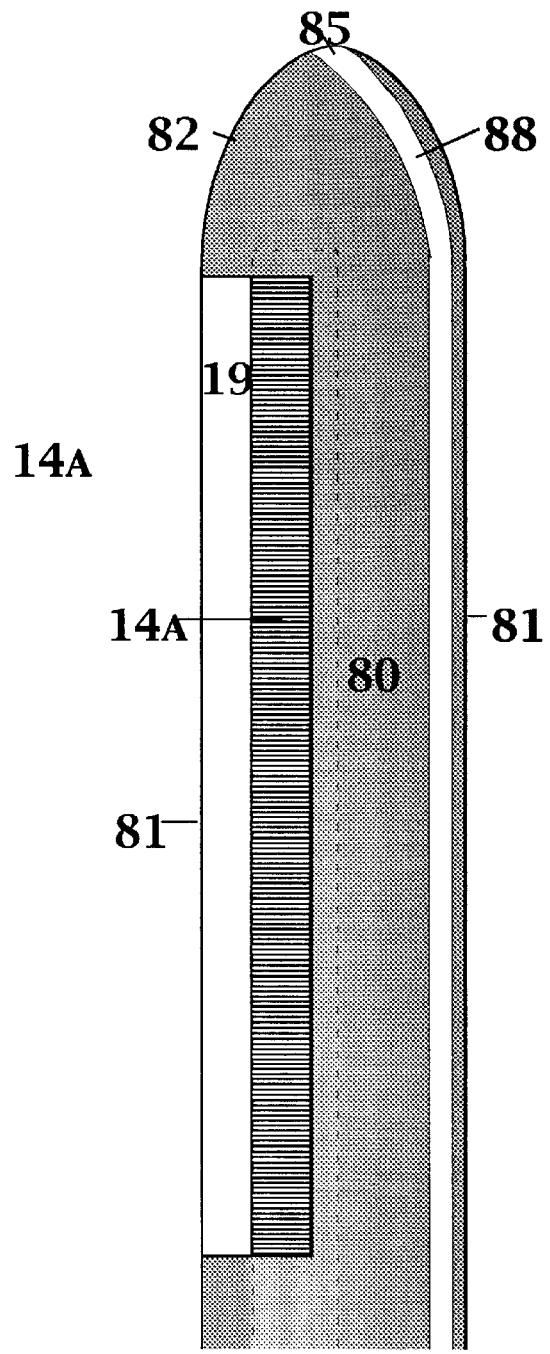
FIG. 16 A
FIG. 16 B

FIG. 19
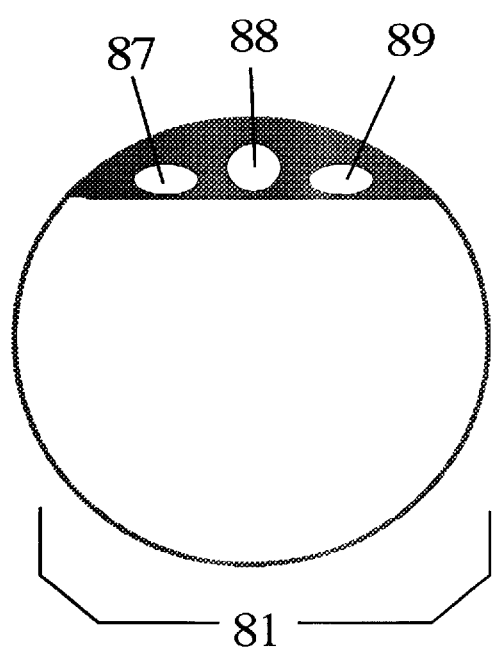
FIG. 20
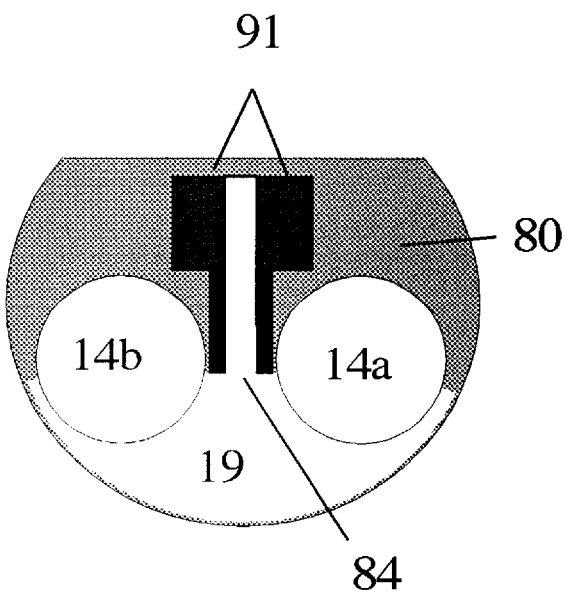
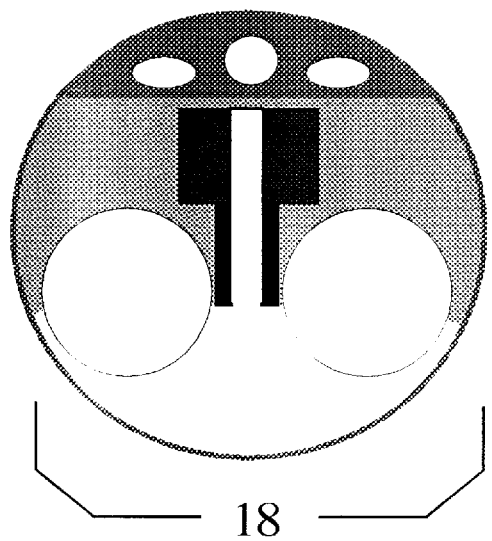
FIG. 21

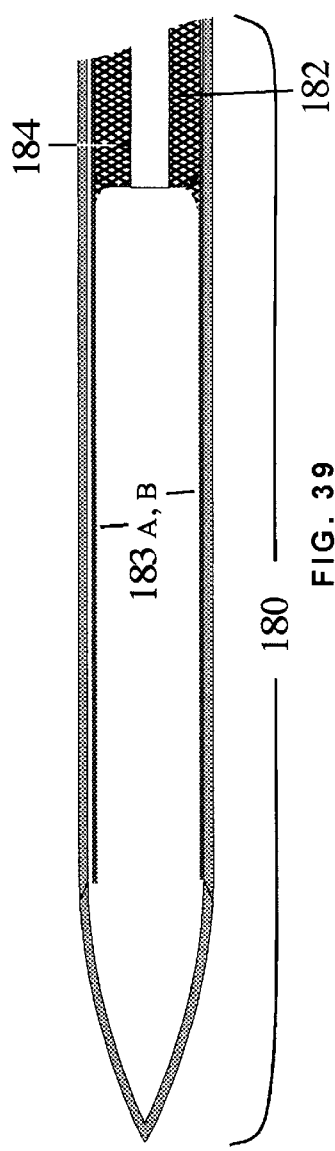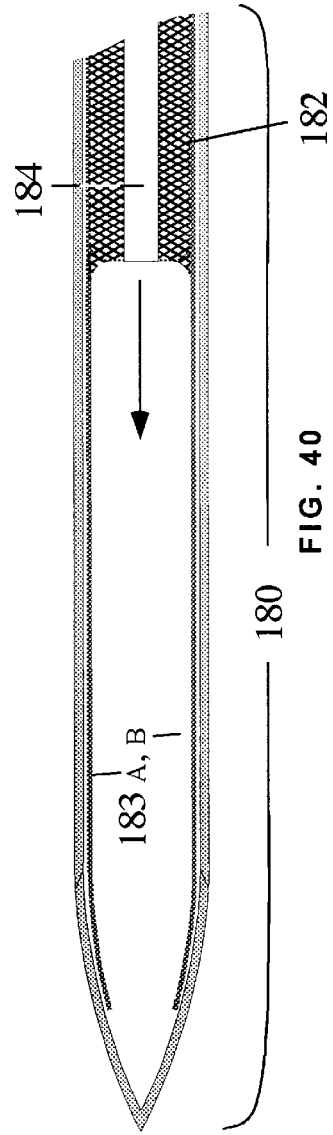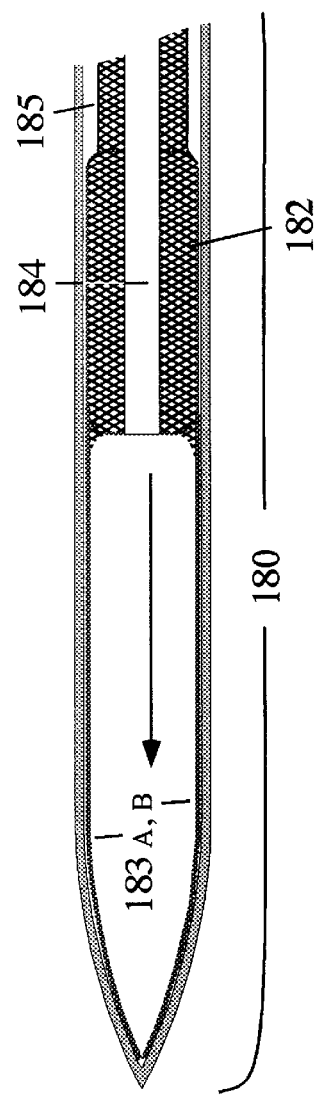

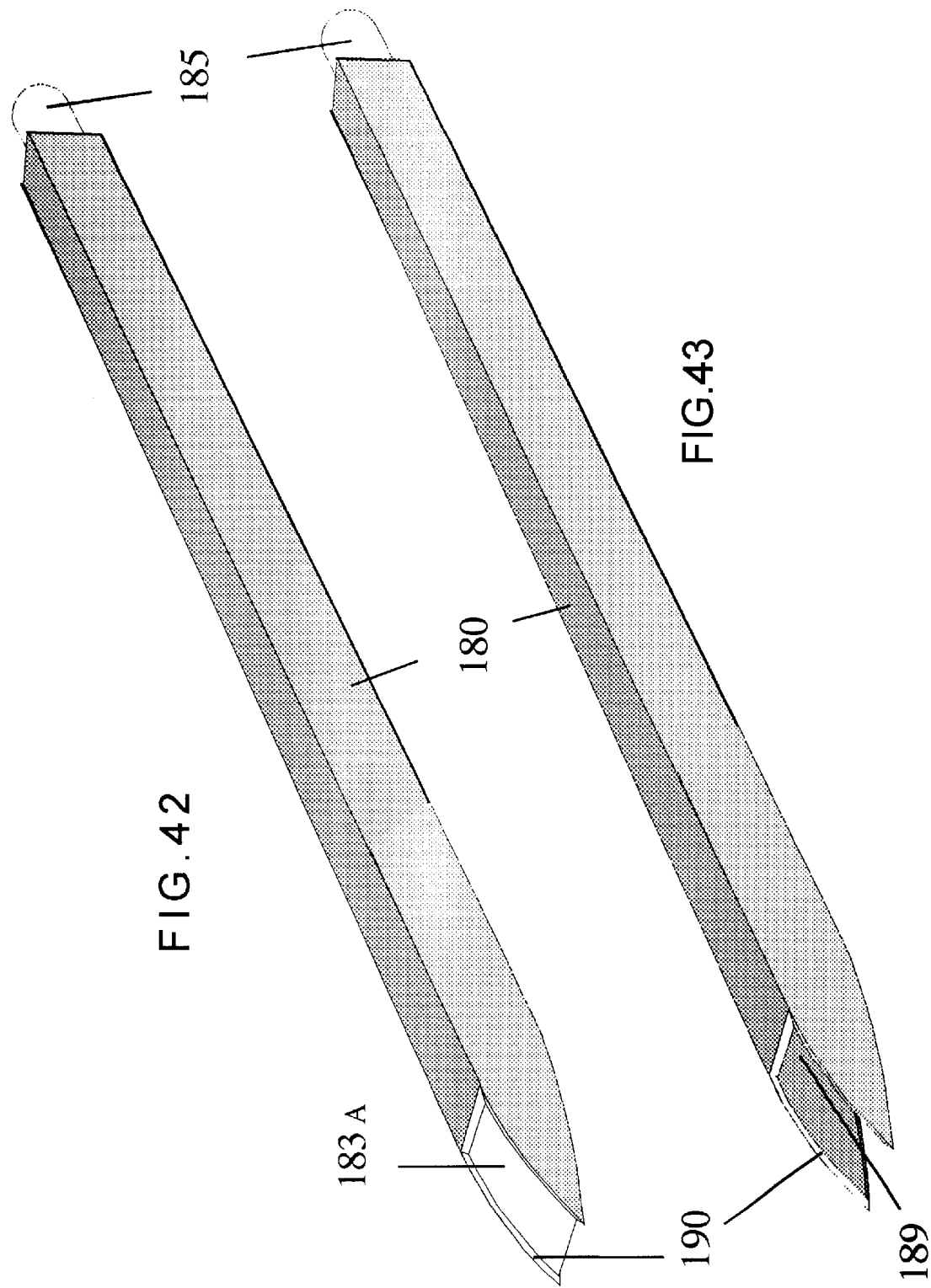

SYSTEM FOR EXAMINING, MAPPING, DIAGNOSING, AND TREATING DISEASES OF THE PROSTATE

CROSS-REFERENCE TO RELATED APPLICATION

This application claims the benefit of U.S. Provisional Application No. 60/362,992, filed Mar. 11, 2002 for "Integrated System for Examination, Diagnosis, Mapping, and Treatment of Prostate Problems."

BACKGROUND OF THE INVENTION

1. Field of the Invention

This invention relates generally to medical devices. It relates particularly to a holistically integrated ultrasonic system and process for examining, mapping, diagnosing, and treating diseases of the prostate gland in a male human, especially prostate cancer.

2. Description of the Related Art

Prostate gland problems are widespread in the male population, especially the older male population. In particular, benign prostatic hyperplasia (BPH) and prostate cancer are all-too-common in men over 50 years of age. Indeed, prostate cancer is the cause of death in about 40,000 men each year, making it the Number Two cancer killer of men in the United States, second only to lung cancer. However, if prostate cancer is detected early and treated effectively, the chance of survival of one afflicted with this disease improves significantly. Unfortunately, methods of detection of prostate cancer employed today are found seriously wanting, even in the hand of the highly skilled, as many early stage cancers still go undetected and/or an undue multiplicity of painful biopsies are required for diagnosis.

In an attempt to enhance the efficiency and efficacy of methods and systems of detection of prostate cancer, medical science turned to ultrasonics, and for several years ultrasonics has been applied in accomplishing diagnostic examinations of the prostate gland of the human male. As examples of advances made in this and related are as are the following U.S. Pat. Nos. 5,282,472; 5,398,690; 5,810,731; 5,952,828; 5,178,147; 5,919,139; 5,952,828; and 6,165,128. Notwithstanding the achievements of these inventions, the fact remains that no examining system or technique presently exists which provides the high degree of resolution and the accompanying precision which are absolutely necessary for an accurate diagnosis of prostate cancer, nor is the required repeatability of result achieved. Moreover, no technique, method, or system of the related art provides a holistically integrated ultrasonic approach which combines examining, mapping, diagnosing, and treating diseases of the prostate gland, especially cancer, in a male human, with a minimum of physical and mental discomfort.

SUMMARY OF THE INVENTION

It is accordingly a primary object of the present invention to obviate the disadvantages presented by systems and processes of the Related Art. This object is achieved, and attending benefits are acquired, by the provision of a holistically integrated ultrasonic system for examining, mapping, diagnosing and treating diseases of the prostate gland in a male human.

The first factor in the holistically integrated ultrasonic system of the present invention is means to reliably detect and map prostate cancer in early stages. However, success in the area of reliable detection and mapping will not be readily accepted and utilized appropriately, unless a second factor is integrated into the system. The second factor (a highly reliable follow-on biopsy or the application of a precisely guided reactive sensor to cancer tissue contact) is the means to reliably confirm the findings of the first factor.

Delivery of an integrated system comprising the above two factors yields opportunities to treat prostate cancer at times when the probability for successful treatment is high. Therefore, the present invention includes a third factor that provides for vastly improving the results of today's treatment modalities, as well as the introduction of new, effective, and patient friendly treatment modalities for prostate cancer in early stages.

To achieve consistent and reliable detection across the total spectrum of prostate cancer conditions, the present invention includes a fourth factor, which is an expert system, which provides the ability to utilize and integrate, in real time, data from several sensor inputs with several analytical techniques (this is not feasible with the limitations of human performance, but is achievable with the present expert system). The fifth factor in the instant system is cost-effectiveness to lower the overall health care cost associated with prostate cancer detection and treatment.

In the operation of the holistically integrated ultrasonic system according to the present invention, the following are applied:

(1) More than one ultrasonic sensor package working together in an integrated manner;
(2) Multiple analytical techniques;
(3) A constant, effective medium for superior ultrasonic sensor performance;
(4) High frequency ultrasound versus the lower frequency used in today's technology;
(5) Level-of-suspicion prostate cancer mapping;
(6) An automated slave biopsy subsystem with precision targeting; and
(7) A design philosophy to create a friendly patient and doctor experience.

As a result, the present invention has the capacity to:

(1) Provide early prostate cancer detection when the cancer or cancers are small;
(2) Automatically and clearly identify what has changed between successive examinations;
(3) Track treatment impact in real time for certain treatment modalities, and for others, to provide tracking over different time periods;
(4) Provide new, patient friendly, treatment options;
(5) Produce the matching of system output with pathology findings as proof of system performance.

BRIEF DESCRIPTION OF THE DRAWINGS

FIGS. 3A, 3B and 3C are cross-sectional schematic showing in the beam patterns emanating from each ultrasound system (transrectal and transurethral) separately and then in the actual overlapping pattern. Each pattern is superimposed on an outline of a diseased prostate showing the bi-directional scanning of a tumor section lying in the scan plane.

FIGS. 7A, 7B and 7C show the same three views of the chair, but define the locations of the field generating elements for the magnetic position sensing system used in conjunction with the floating transrectal probe, shown in FIG. 8.

FIGS. 16A and 16B are sectional, schematic views showing a front pseudo-perspective and a side cross sectional view of the transrectal probe.

FIGS. 19, 20 and 21 are sectional, schematic views showing three cross sections through the transrectal probe.

FIG. 30 shows a macerating cutter deployed within the tumor. FIG. 31 shows the tool reducing the volume containing the tumor to a liquid state. FIG. 32 shows the liquid extracted leaving a cavity where the tumor was. FIG. 33 shows the cavity filled with a collagen gel derived from the patients own tissues and carrying the appropriate dosage of anti-cancer drugs.

FIGS. 39, 40 and 41 are a three-part cutaway, side view of the biopsy needle showing how the forward movement of the slider pushes the blades to follow the curved guides and meet at the needle tip. The needle is then extracted containing the tissue sample.

FIGS. 42 and 43 are a set of perspective drawings of the square-end cutting biopsy needle. FIG. 43 shows the open end of the needle as it would appear during the harvesting phase of a biopsy. FIG. 42 shows the cutting blades fully extended to cut off and enclose the tissue sample.

DETAILED DESCRIPTION OF THE INVENTION

Figure 1:
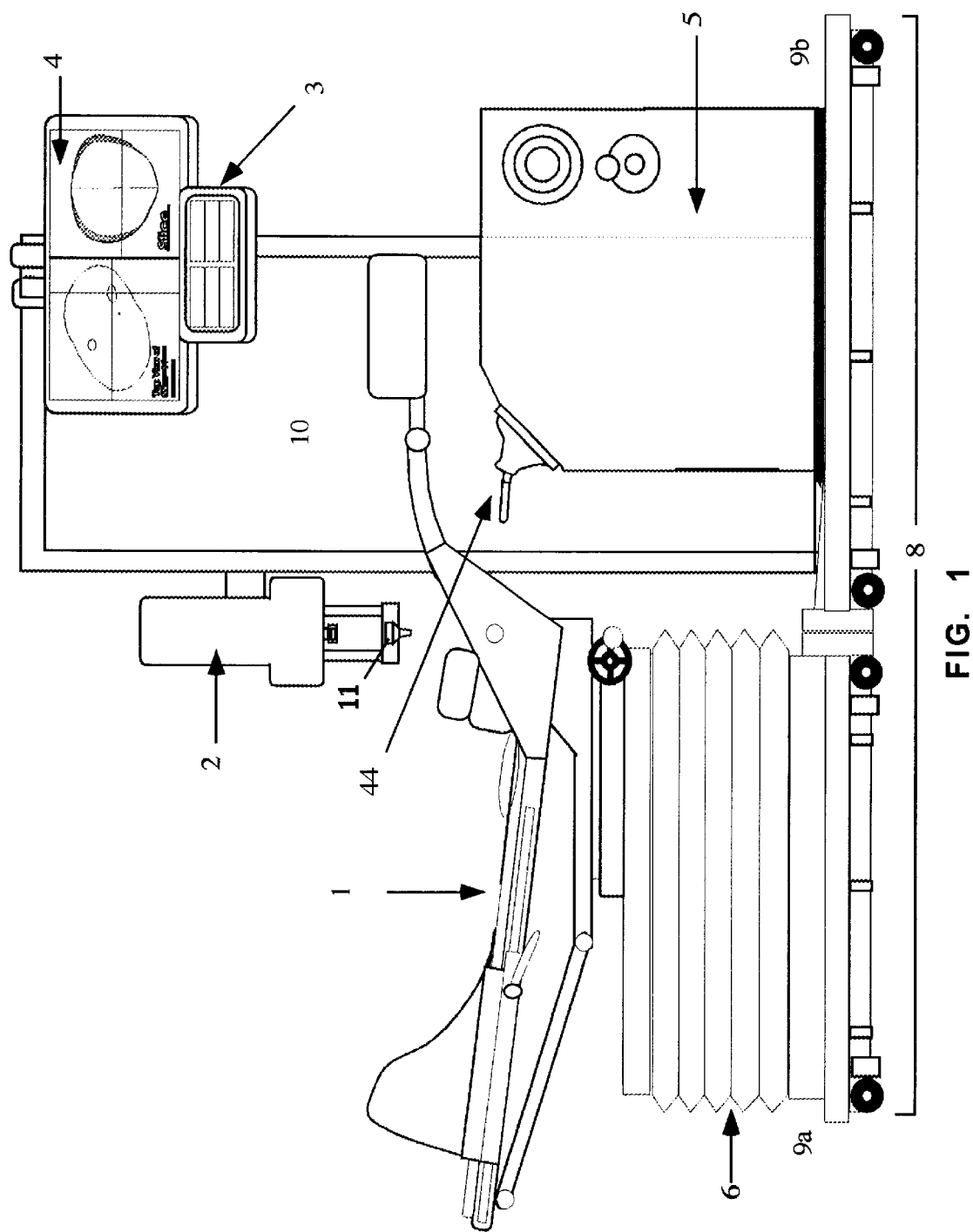
FIG. 1 is a schematic view of the overall system of the present invention, showing the major elements thereof.

Following is a listing of elements constituting the system of the present invention, along with their corresponding reference numerals, as employed in the accompanying drawings.

| | |
|---|---|
| 1 | patient chair |
| 2 | transurethral actuation mechanism |
| 3 | control panel |
| 4 | data display monitor |
| 5 | transrectural actuation mechanism |
| 6 | chair vertical movement |
| 7 | chair angle adjustment mechanism |
| 8 | overall urotech system |
| 9 | a, b duplex support structure a) chair b) transrectal system |
| 10 | electronics cabinet, including software package |
| 11 | transurethral probe support arm |
| 12 | foley balloon on transurethral catheter |
| 13 | transurethral catheter |
| 14 | a, b dual transrectal ultrasound scanners |
| 15 | ultrasound scan beam emitted by transurethral ultrasound scanner |
| 16 | ultrasound scan beam emitted by transrectal ultrasound scanners |
| 17 | chair pivot |
| 18 | transrectal ultrasound probe tip (entire) |
| 19 | frontal cavity within 18 |
| 20 | support plate for chair pivot |
| 21 | a, b, chair hip fence adjusters |
| 22 | a, b chair hip fences |
| 23 | lateral chair adjustment |
| 24 | chair angle adjustment driver |
| 25 | chair saggital axis pivot point |
| 26 | in chair dynamic elastography exciters |
| 27 | belt mounted dynamic elastography exciters |
| 28 | belt |
| 29 | a, b hip fence mounted dynamic elastography exciters |
| 30 | stiffness node |
| 31 | representational dynamic elastography exciters |
| 32 | node showing movement in response to impinging pressure wave |
| 33 | floating transrectal probe umbilical |
| 35 | magnetic drive coils for magnetic position sensing system |
| 36 | magnetic field emitted by said coils |
| 38 | floating transrectal probe |
| 40 | a, b magnetic position sensing coils in floating trausrectal probe |
| 41 | prostate |
| 42 | urinary bladder |
| 43 | rectum |
| 44 | transrectal probe body (entire) |
| 45 | biopsy needle |
| 46 | tumor |
| 47 | transurethral ultrasound scanner |
| 48 | a, b bioimpedance sensing coils |
| 50 | tip of transurethral fiber optic viewer |
| 51 | head of penis |
| 53 | catheter feeder |
| 54 | water line to catheter feeder |
| 55 | transurethral video camera |
| 56 | transurethral fiber optic viewer |
| 57 | transurethral water line luer fitting |
| 60 | transurethral ultrasonic scanner movement |
| 61 | water bolus |
| 62 | urethra |
| 63 | upper sphincter of prostate |
| 64 | lumen of catheter |
| 69 | distal opening of catheter |
| 70 | instrument port of catheter feeder |
| 71 | sealing 0 ring of catheter feeder |
| 72 | luer fitting of catheter feeder |
| 73 | push in latch of catheter feeder |
| 74 | catheter coupler of catheter feeder |
| 80 | transurethral probe support structure |
| 81 | transrectal probe condom cover |
| 82 | head of condom cover |
| 83 | gimbal of needle guide |
| 84 | slot driver for transrectal dynamic elastography exciter |
| 85 | distal opening in condom head-for transrectal-fiber optic viewer |
| 86 | distal opening of water fill line |

-continued

| | |
|---|---|
| 87 | distal opening of air bleed line |
| 88 | lumen of fiber optic viewer passage |
| 89 | lumen of water line |
| 90 | lumen of air bleed line |
| 91 | driver for slot firing dynamic elastography exciter |
| 92 | water supply |
| 95 | water supply line into condom |
| 98 | seal around fiber optic viewer |
| 99 | transrectal fiber optic viewer |
| 100 | transrectal video camera |
| 101 | a, b ultrasound beams emitted by transrectal ultrasound scanners 14a, b |
| 102 | acoustic shadow |
| 103 | bleed air outlet catch container |
| 104 | thermal needle |
| 105 | volume to be necrotized |
| 109 | transrectal docking support structure |
| 110 | inner docking cone |
| 111 | lower magnetic latch |
| 112 | upper magnetic latch |
| 113 | outer docking cone |
| 120 | slaved biopsy device support structure |
| 121 | rotary movement |
| 122 | angular movement |
| 123 | depth of penetration movement |
| 124 | needle drive |
| 125 | needle guide |
| 126 | slaved biopsy mechanism cover |
| 130 | macerating needle |
| 131 | macerating flail |
| 132 | cavity created by macerating flail |
| 133 | cavity filled with gel |
| 135 | collapsed cavity |
| 180 | endcutting biopsy needle (entire) |
| 181 | cross section of square needle |
| 182 | square slider |
| 183 | a, b tissue cuffing blades on square slider |
| 184 | pressure relief lumen |
| 185 | flexible push rod |
| 186 | a, b, c side view cutaway of needle showing movement of the tissue cutting capsule with the blades following the curve of the tip and meeting to shear off tissue sample. |
| 187 | a, b views of the tip of the needle showing details of the opening and the tapered edge fence along which the tissue cutting blades run. |
| 188 | alternative curved needle configuration. |

Referring now to the drawings, FIG. 1 is a schematic view of overall system showing the major elements thereof. The entire system is identified as 8. Subsystems are as follows: the adjustable, swiveling patient chair 1 is supported on vertical movement 6 which is in turn mounted on 9a one of the duplex support structures. The second duplex support structure 9b carries the transrectal actuation system designated as 5. 5 is surmounted by the transrectal probe dock shown with transrectal probe 44 latched in place. Located behind and in fixed relationship to 9a, b is the electronic cabinet 10. On the end of cabinet 10, which is adjacent to the position of the patient's groin area is mounted the transurethral actuation system 2. Said transurethral actuation system 2 has 3 degrees of freedom: it can be pulled forward to intersect the central axis of the patient. It can be moved several inches along that axis to accommodate patient variability. It can also be moved in the vertical plane to permit the distal end of the transurethral drive support arm 11 to be positioned in the proper relationship to the head of the patient's penis. On the forward face of cabinet 10 is mounted data display monitor 4 and control panel 3. Both monitor 4 and control panel 3 are at the distal end of an adjustable arm, permitting them to be positioned at the ideal position for the physician.

Figure 2:
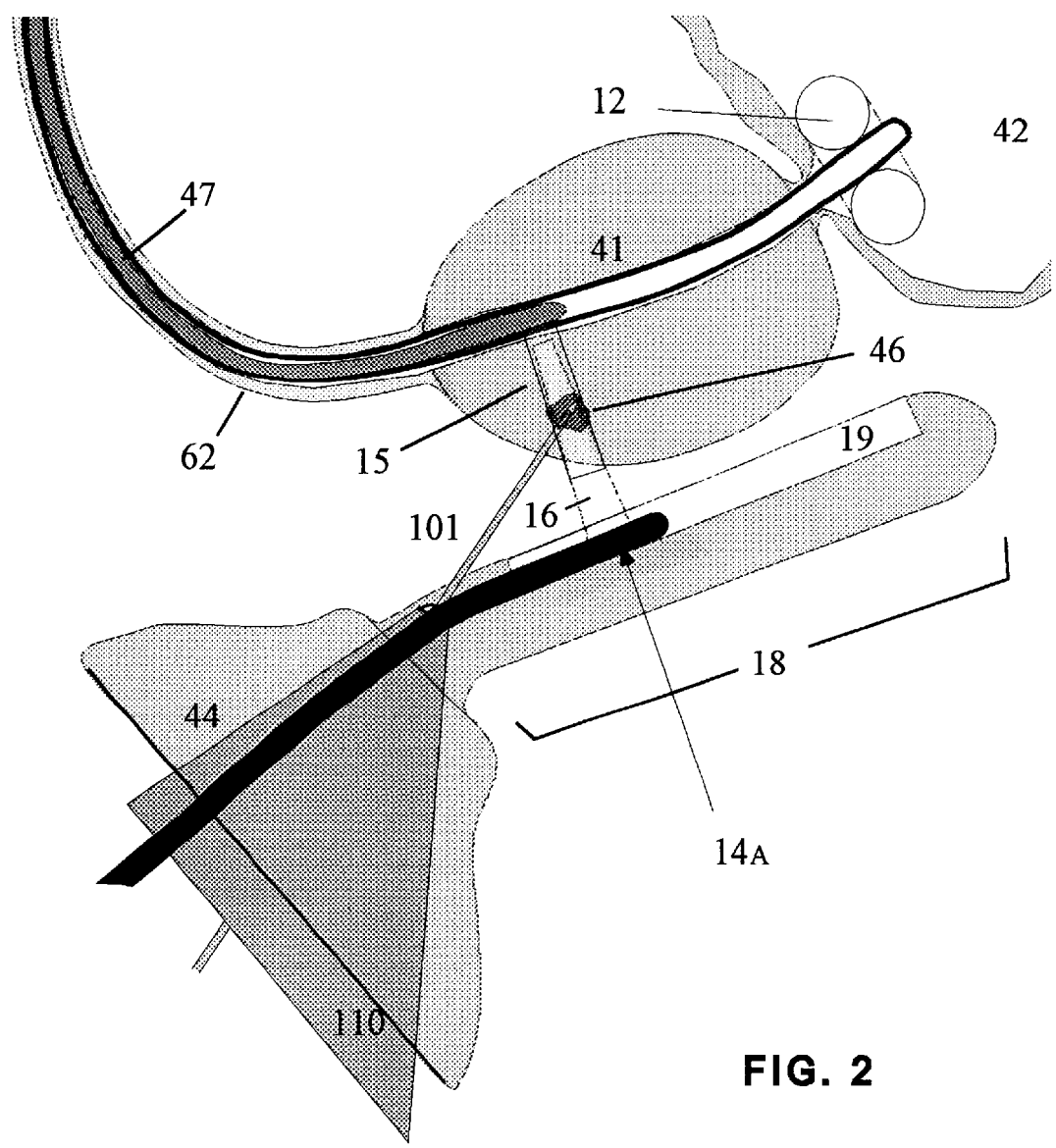
FIG. 2 is a sectional, schematic, anatomical view showing both transrectal and transurethral systems in place in the rectum and the prostatic urethra respectively. It also shows an overlapping beam pattern from the two ultrasound systems with a detected tumor being sonically illuminated from both sides. It further shows a slaved biopsy needle deployed into said tumor.

FIG. 2 is a sectional, schematic, anatomical view showing the probe portion 18 of transrectal probe body 44 in place in the rectum 43 and adjacent to the prostate 41. The transrectal probe body 44 is shown as a transparency to show the one of the transrectal scanners 19a, b passing through the base and into the cavity 20. The second transrectal scanner 19b is directly behind 19a on the other side of the probe centerline. The transparency of 44 also shows the locating cone/gimbal support 88 within probe body 44. The transurethral scanner 47 moves within the transurethral catheter 52 which has been inserted by the physician through the urethra 61 and the prostate 41 into urinary bladder 42 where it is anchored by foley balloon 12. Overlapping ultrasound beams 15–16 are emitted by transurethral scanner 47 and transrectal scanner 14 respectively. A tumor 46 is shown in the beam path and being scanned from both sides. FIG. 2 also shows a biopsy needle 45 deployed through gimbal 83 into said tumor.

FIGS. 3A, 3B, and 3C are cross-sectional schematics showing the beam patterns 16, 15 emanating from each ultrasound scanner (transrectal 14 and transurethral 47) separately and then in the actual overlapping pattern. Each pattern is superimposed on an outline of a diseased prostate 41 showing the bi-directional scanning of a tumor section 46 lying in the scan plane.

Figure 4A:
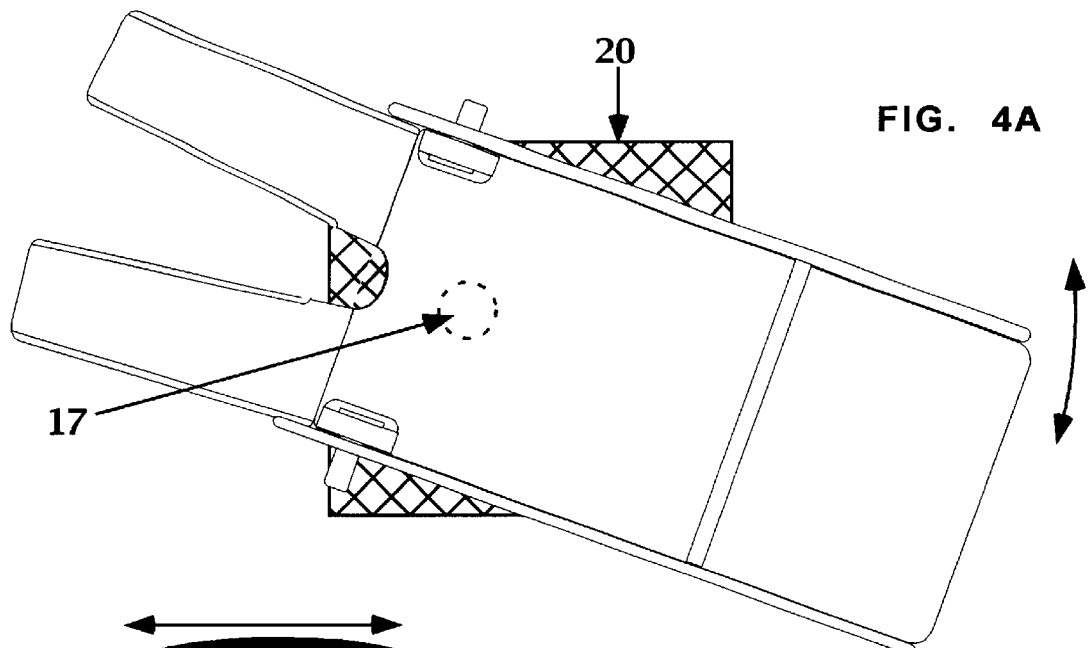
FIGS. 4A, 4B and 4C are a schematic showing a top view, a side view and a cross-sectional view of a chair mechanism according to the present invention.
Figure 4B:
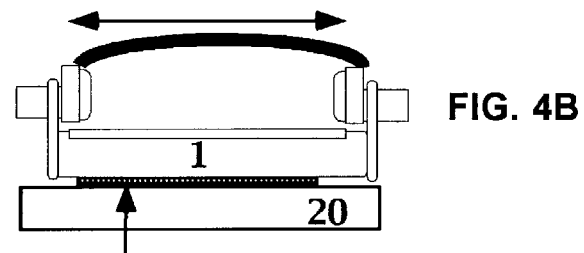
Figure 4C:
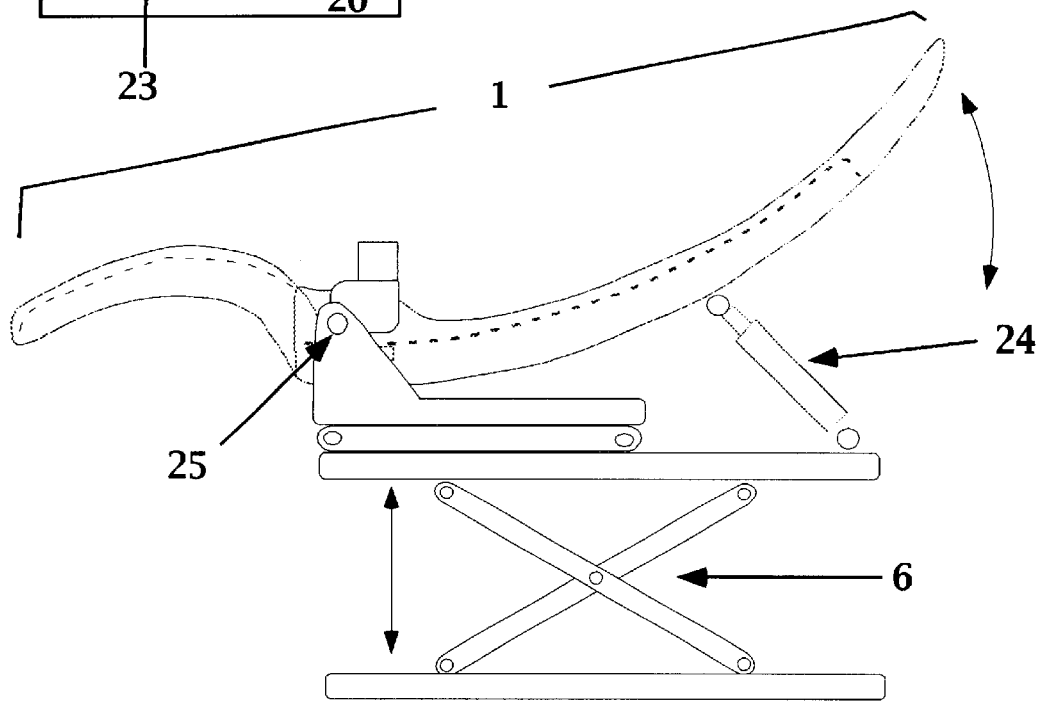

FIGS. 4A, 4B and 4C are schematics showing a top view, a side view and a cross-sectional view of the patient chair 1 together with its associated mechanisms. FIG. 4A shows the chair 1 pivoting around pivot 17 which is in turn mounted on support platform 11. FIG. 4B shows the lateral movement 23 for adjusting the patient position relative to center line. FIG. 4C shows the elevation mechanism 24 and the tilting action of the chair 1 proper.

Figure 5A:
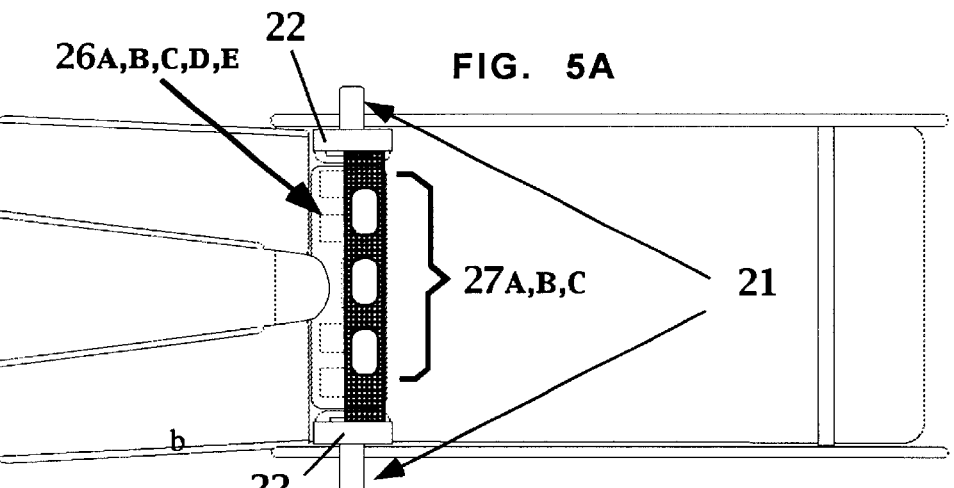
FIGS. 5A, 5B and 5C show the same three views of the chair, but define the locations of the multiple actuators which produce the excitation sound waves used for the dynamic elastography feature according to the present invention.
Figure 5B:
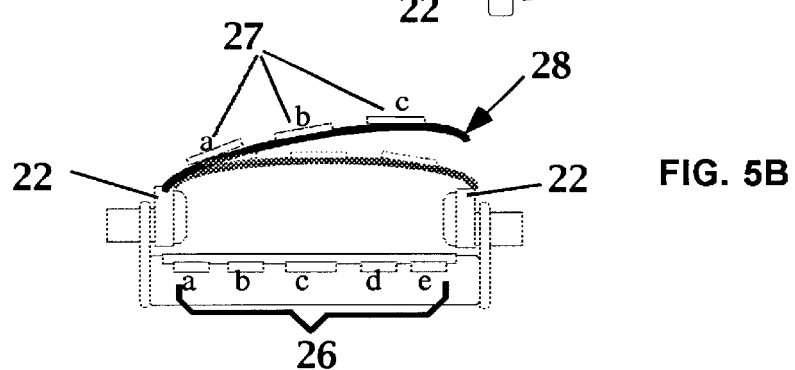
Figure 5C:
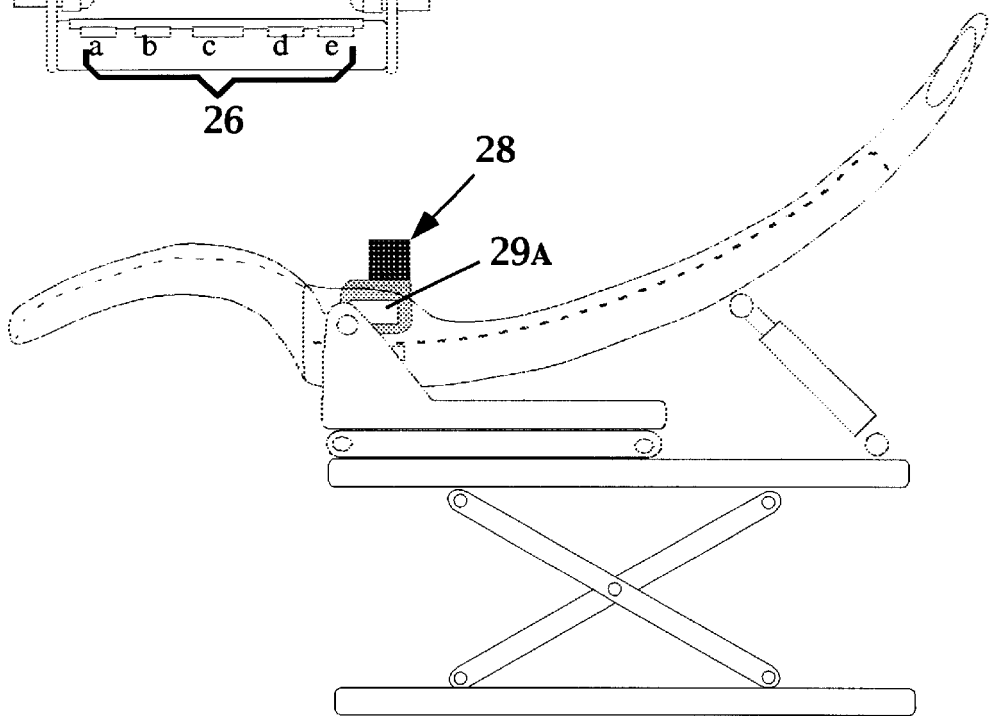

FIGS. 5A, 5B and 5C show the same three views of the chair but define the locations of the multiple actuators: 26a, b, c, d, e in the chair back, 27a, b, c in the belt, 28 and 29a, b which are in the hip fences, and 22a, b, c which produce the excitation sound waves used for the dynamic elastography feature.

Figure 6B:
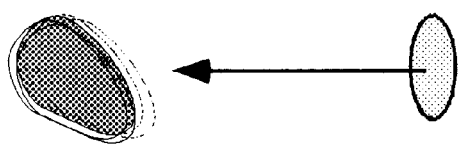
FIG. 6 is an illustration of the impingement of elastography exitation pressure waves arriving at an area of differential stiffness, so that by varying the direction, frequency and power of the impinging waves, it is possible to maximize the ultrasonically detectable differential vibration of a tumor thus produced.
Figure 6:
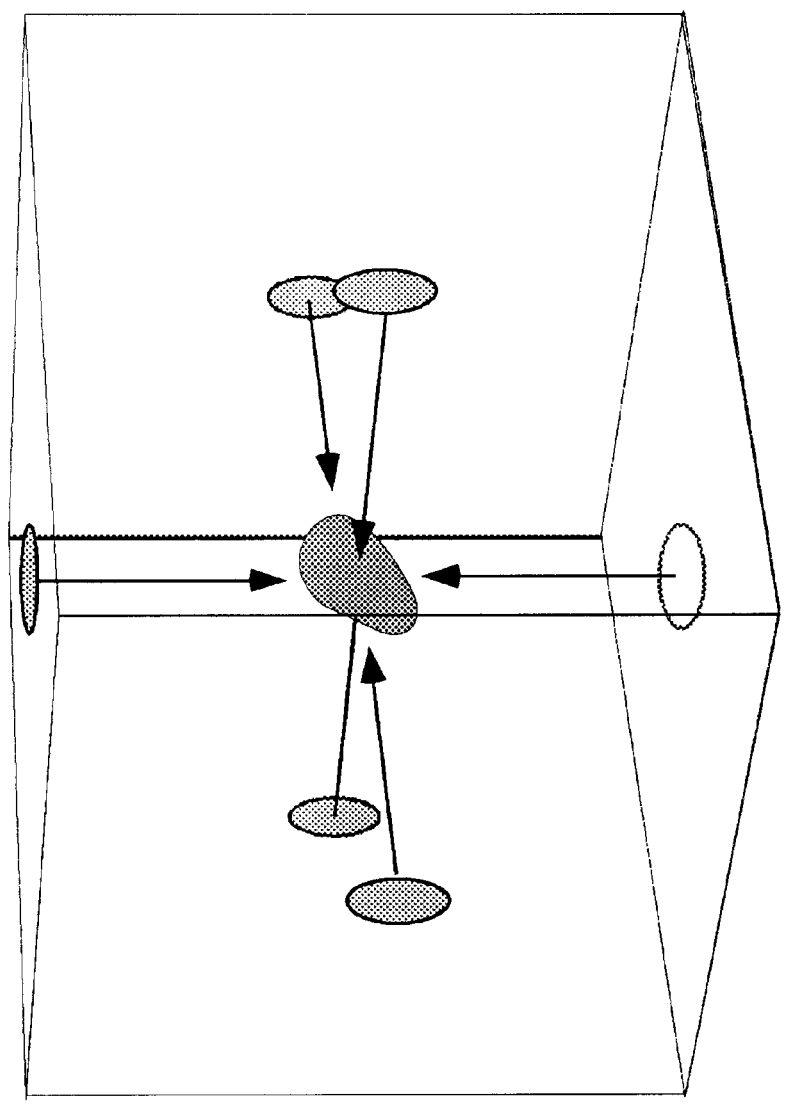

FIG. 6 shows the impingement of elastography pressure waves arriving at an area of differential stiffness, so that by varying the direction, frequency, and power of the impinging waves, it is possible to maximize the ultrasonically detectable differential vibration of the tumor.

Figure 8:
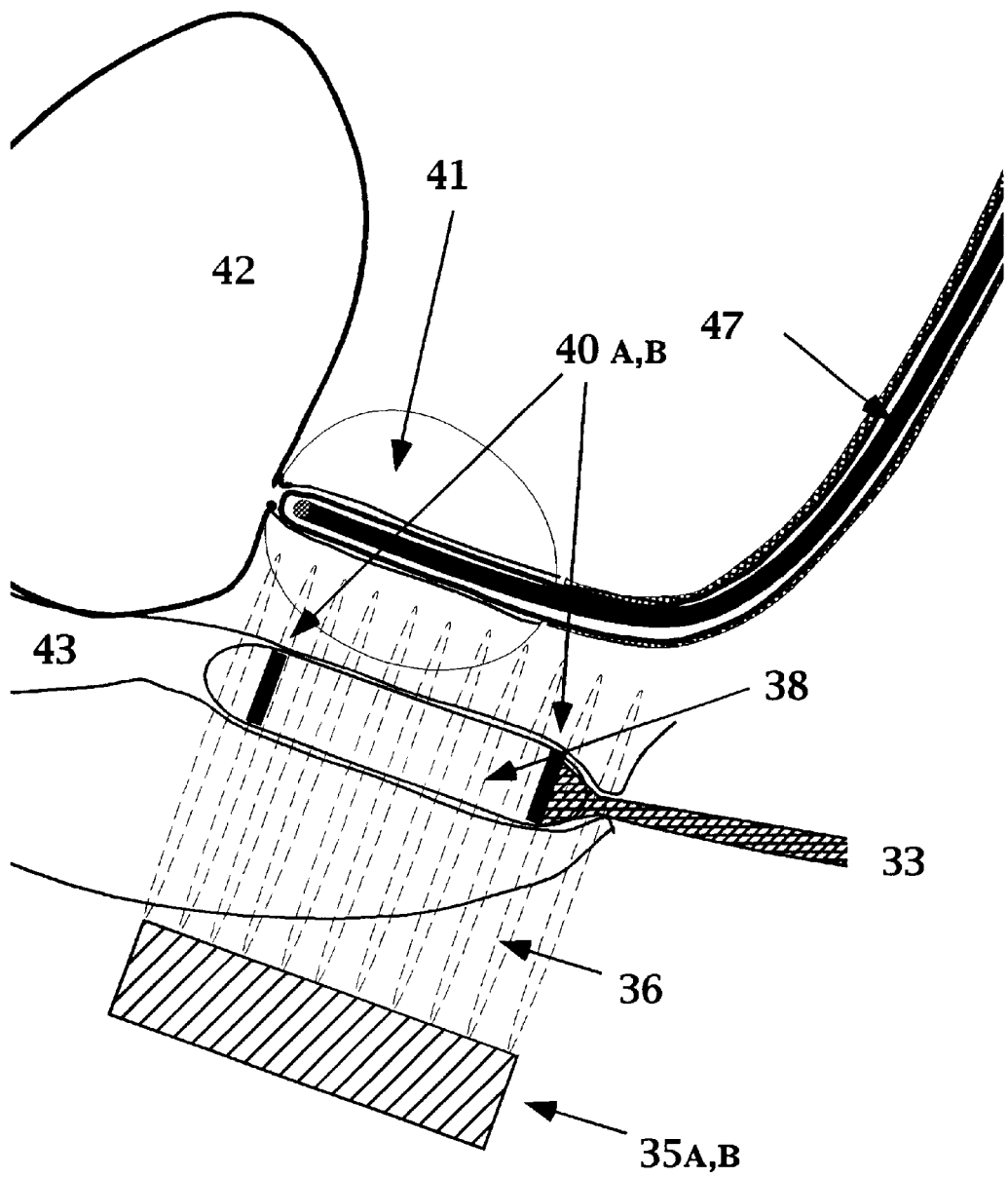
FIG. 8 is a sectional, schematic, anatomical view showing the floating transrectal probe in situ. The drawing shows the relationship of the magnetic field produced by generating elements to the sensing coils located at either end of the floating probe.

FIGS. 7A, 7B and 7C show the same three views of the chair as in FIGS. 5A–C but define the locations of the field generating elements 35a, b for the magnetic position sensing system used in conjunction with the floating transrectal probe 38 which will be shown in FIG. 8.

FIG. 8 is a sectional, schematic, anatomical view showing the above mentioned floating transrectal probe 38 in situ. The drawing shows the relationship of the magnetic field 36 produced by above said generating elements to the sensing coils 40a, b located at either end of said floating probe 38.

Figure 9:
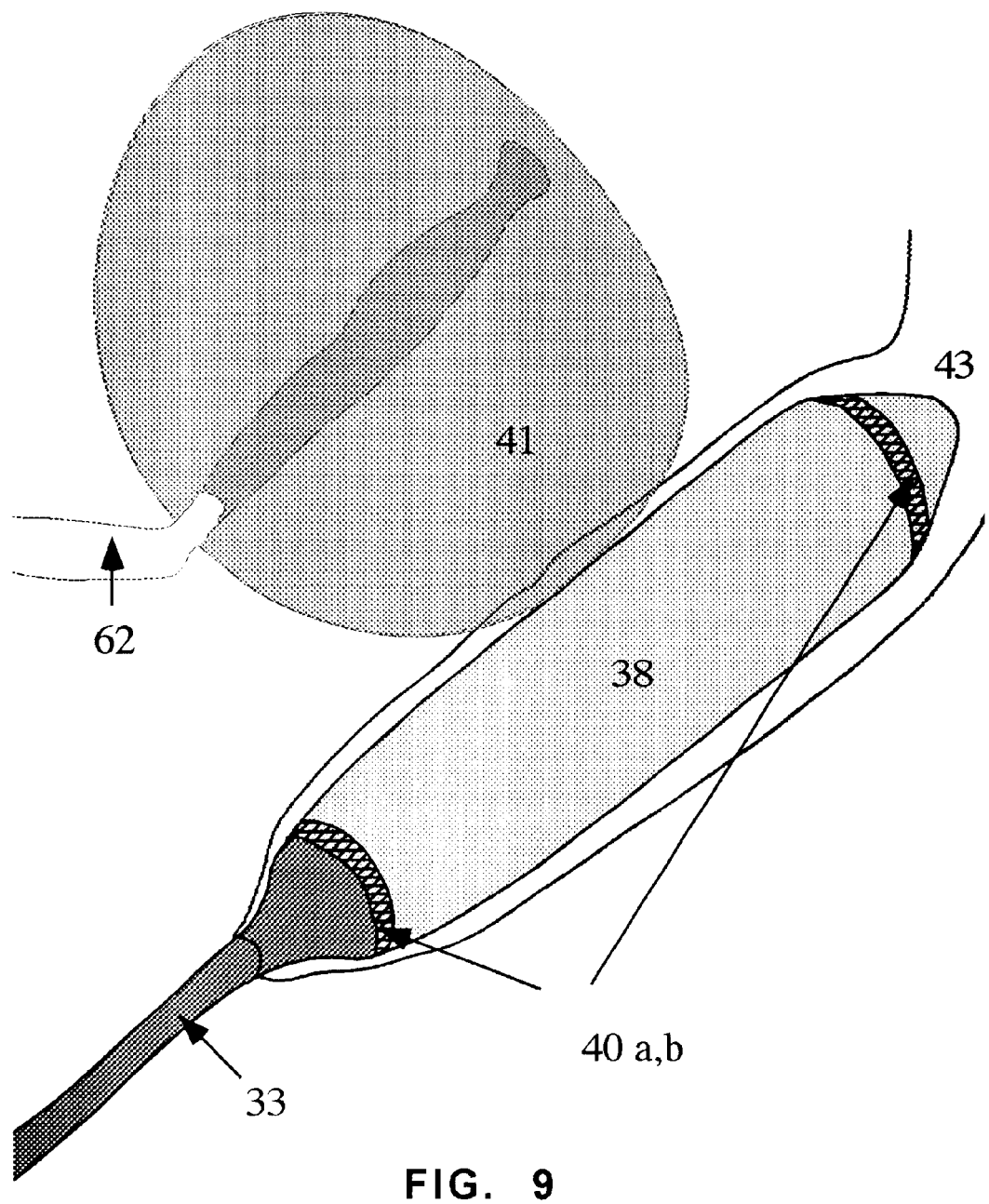
FIG. 9 is a sectional, schematic, anatomical view showing the floating transrectal probe in situ within the body.

FIG. 9 is a sectional, schematic, anatomical view showing said floating transrectal probe 38 in situ within the rectum 43. The drawing particularly references the location of the two magnetic sensing coils 40a, b relative to the probe body and the attachment of said probe body to the umbilical 33.

Figure 10:
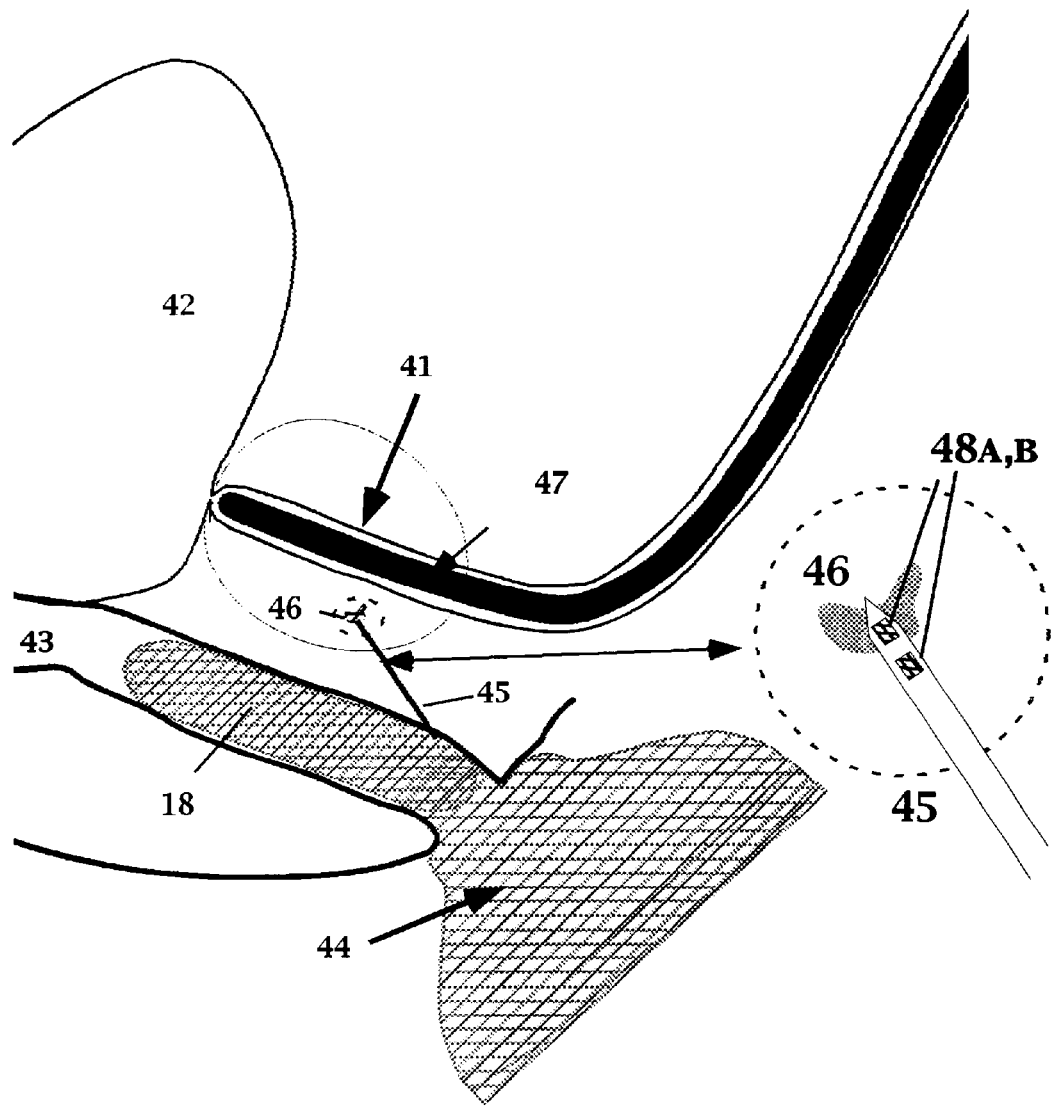
FIG. 10 is a sectional, schematic, anatomical view showing both the transrectal and the transurethral probes in situ with the special diagnostic needle deployed into a detected tumor.

FIG. 10 is a sectional, schematic, anatomical view showing both the transrectal probe tip 18 and the transurethral probe 47 in situ with a special diagnostic needle 45 deployed into a detected tumor 46. Said diagnostic needle as shown in the enlarged inset carries a pair of detection coils 48a, b that measure the effective radio-frequency bio-impedance of the tumor. Said bioimpedance has been shown to vary with the stage of the tumor.

Figure 11:
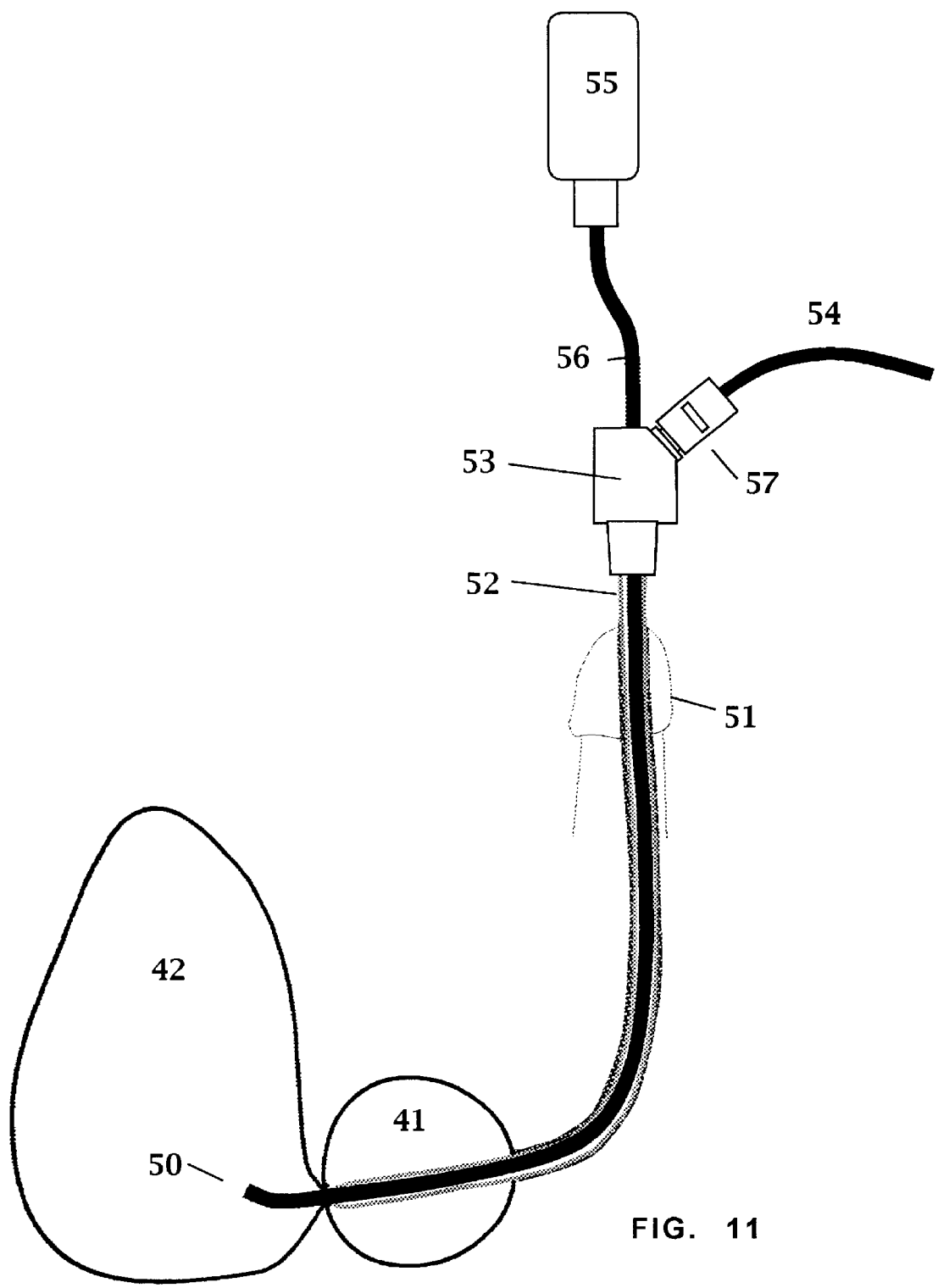
FIG. 11 is a sectional, schematic, anatomical view showing the transurethral catheter/catheter feeder assembly in situ. The drawing shows the fiber optic viewer/guide in situ within the catheter and protruding into the urinary bladder. The upper end of the fiber optic terminates in a small optical pickup which feeds a display used by the doctor for guidance and to assist in diagnosis. The water feed line is shown attached to the catheter feeder.

FIG. 11 is a sectional, schematic, anatomical view showing the transurethral catheter 52 and catheter feeder 53 in situ. The drawing shows the fiber optic viewer/guide 56 in situ within the catheter 13 and protruding into the urinary bladder 42. The upper end of the fiber optic terminates in a small video camera 55 which feeds a display used by the doctor for guidance and to assist in diagnosis. The water feed line 54 is shown attached to the catheter feeder 53, via luer fitting 57.

Figure 12:
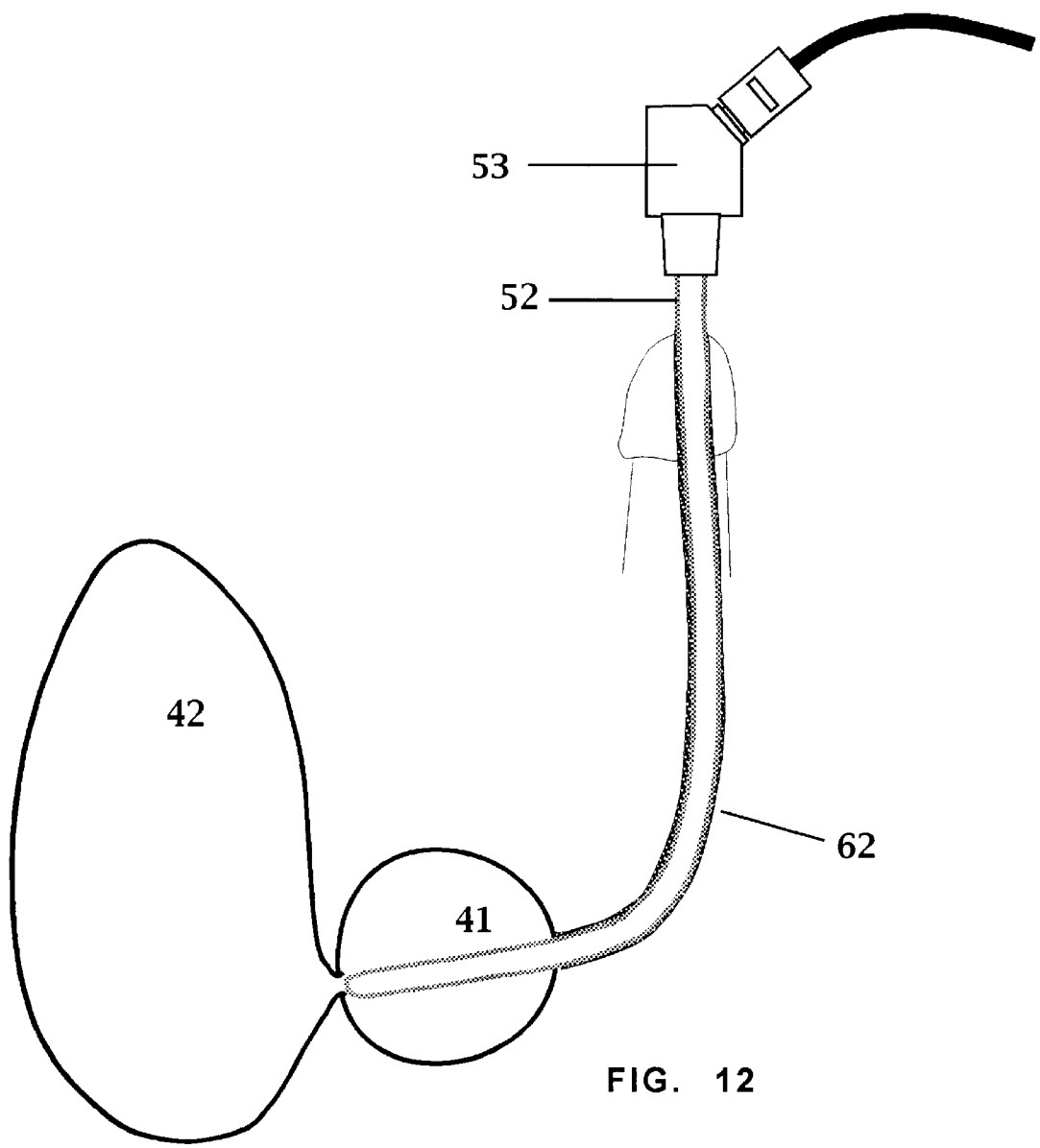
FIG. 12 is a sectional, schematic, anatomical view showing the same view as in FIG. 11 but with the fiber optic viewer/guide withdrawn from the catheter/catheter feeder assembly.

FIG. 12 is a sectional, schematic, anatomical view showing the same view as in FIG. 11, but with the fiber optic viewer/guide withdrawn from the catheter/catheter feeder assembly.

Figure 13:
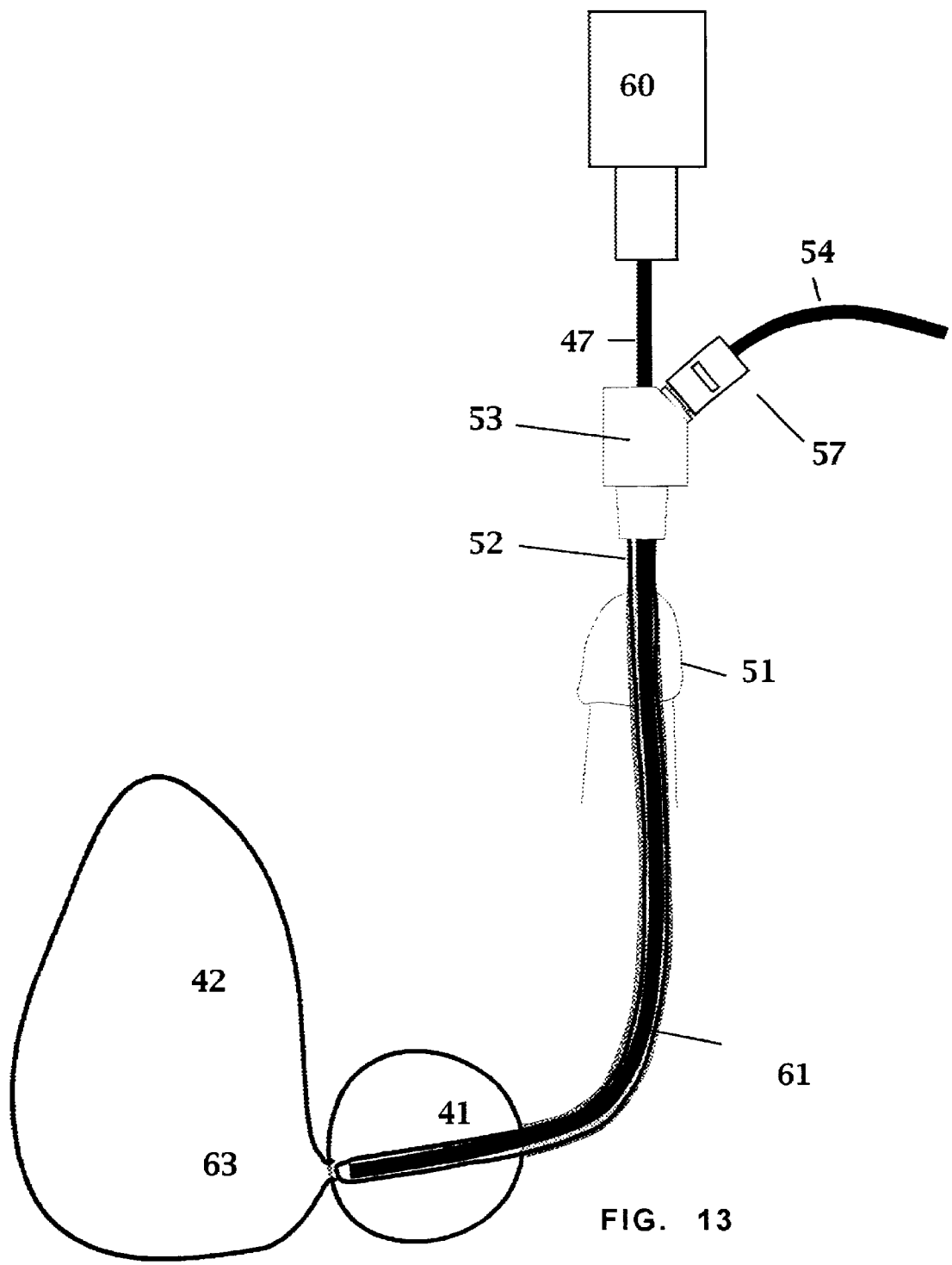
FIG. 13 is a sectional, schematic, anatomical view showing the same view as in FIG. 12 but with the transurethral ultrasound probe inserted through the catheter feeder into the catheter.

FIG. 13 is a sectional, schematic, anatomical view showing the same view as in FIG. 12, but with the transurethral ultrasound probe 47 inserted through the catheter feeder into the catheter 52 as far as the correct starting position at the distal end of the catheter just within the upper sphincter of the prostatatic urethra 53.

Figure 14:
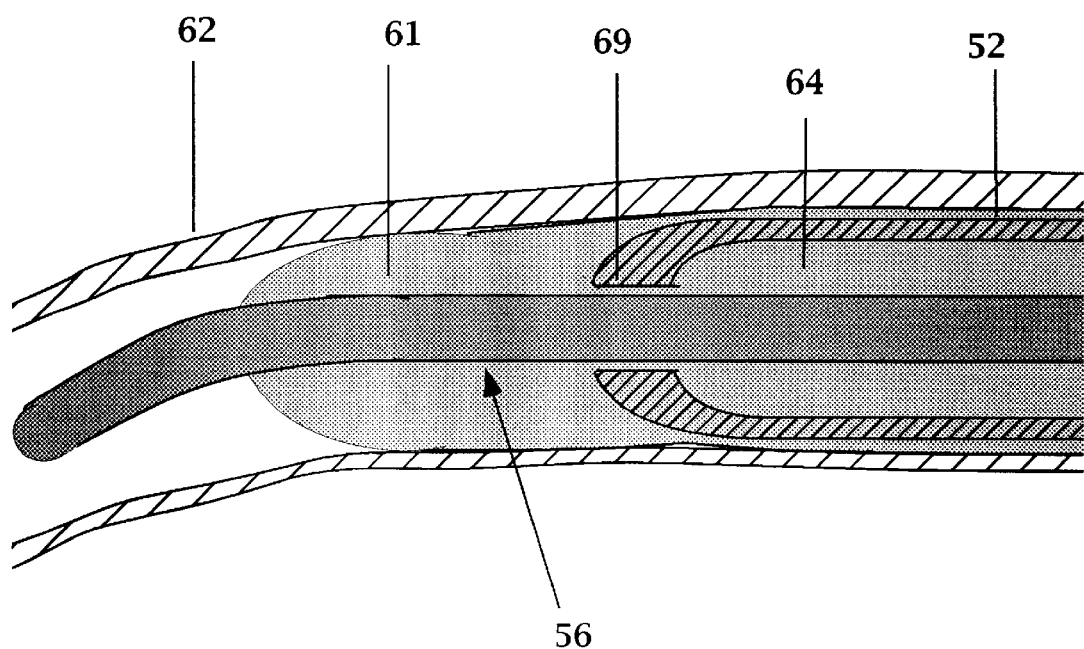
FIG. 14 is a sectional, schematic, anatomical view showing a close-up cross section of the catheter within the urethra. The distal opening of the catheter is shown with the fiber optic viewer/guide protruding through the distal opening.

FIG. 14 is a sectional, schematic, anatomical view showing a close-up cross section of the catheter 13 within the urethra 62. The distal opening of the catheter 69 is shown with the fiber optic viewer/guide 56 protruding through said distal opening 69. The water filling the catheter 64 and being extruded through said distal opening to form a leading bolus 61 is shown.

Figure 15:
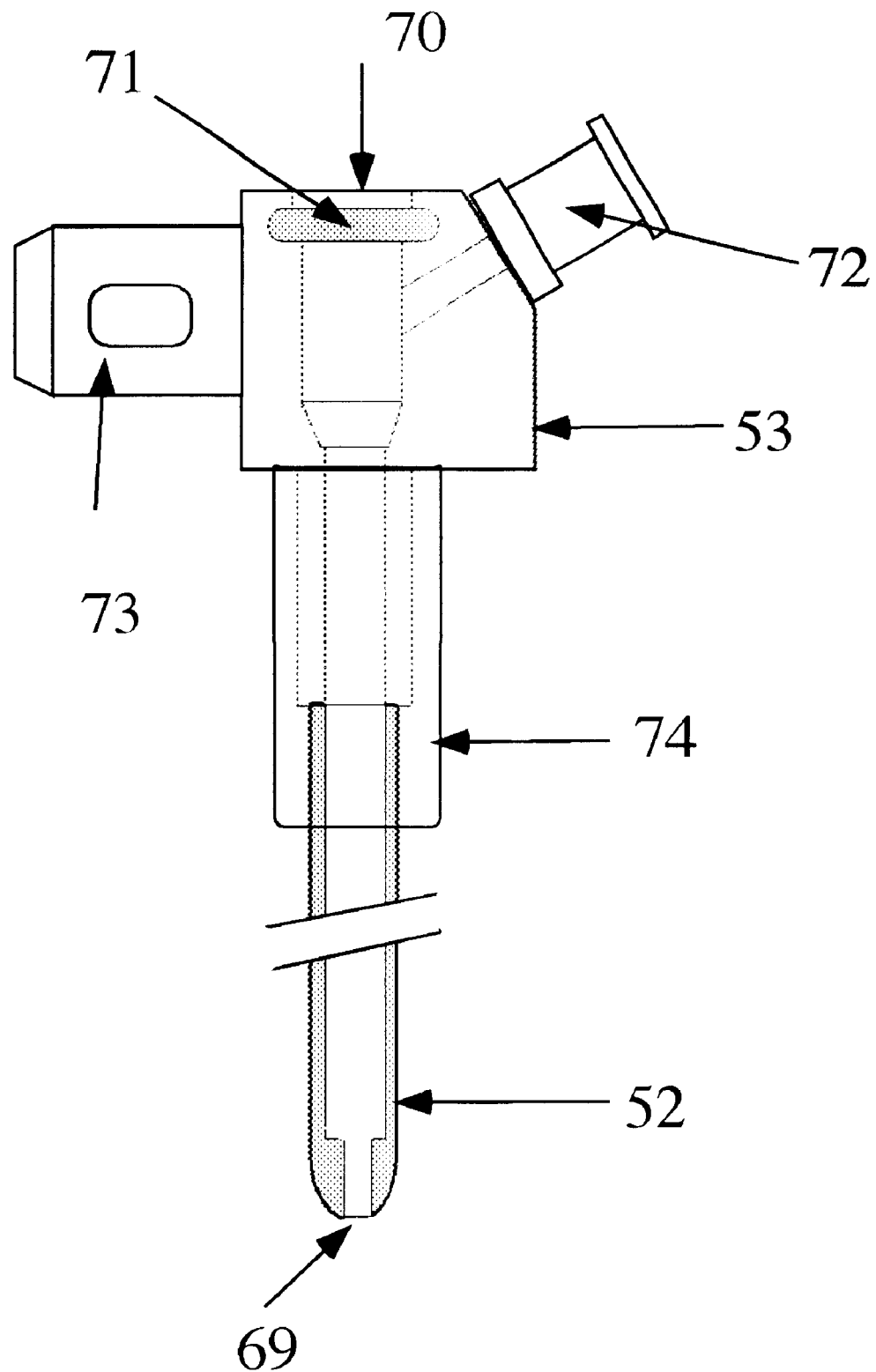
FIG. 15 is a sectional, schematic, anatomical view showing the details of the catheter/catheter feeder assembly.

FIG. 15 is a sectional, schematic view showing the details of the catheter 13/catheter feeder 53 assembly. Shown are the passageways, the luer fitting for the water inlet 72, the sealing O-ring 71 which minimizes water leakage around inserted probes, and the push-in latch 73 used to attach the catheter feeder to the receptacle at the distal end of the transurethral locating arm.

FIGS. 16A and 16B are sectional, schematic views showing a front pseudo-perspective and a side cross sectional view of the transrectal probe 18 general layout. In said front pseudo-perspective view (FIG. 16A) the two complimentary scanning ultrasound systems 14a,b are shown, resident in the forward (towards the prostate) looking cavity/window 19 on the ventral side of the transrectal probe. Said front pseudo-perspective view also shows the slot aperture 84 which is one element of the dynamic elastography multi angle excitation system. Cavity 19 is a cutaway of the front of the rigid probe tip support structure 80 which is shaped to conform to the covering condom 81. The condom covers the entire surface of the probe tip 18 and probe body 44. Housed within the thickened back wall of the condom are lumens to accommodate a fiber optic viewer, a water fill line and an air bleed line, all of which terminate in openings in the end cap of the condom (detailed in FIG. 21). The condom forms the front wall of the cavity 19 which houses the dual ultrasound scanners 14a, b to act as an acoustically transparent window.

Figure 17:
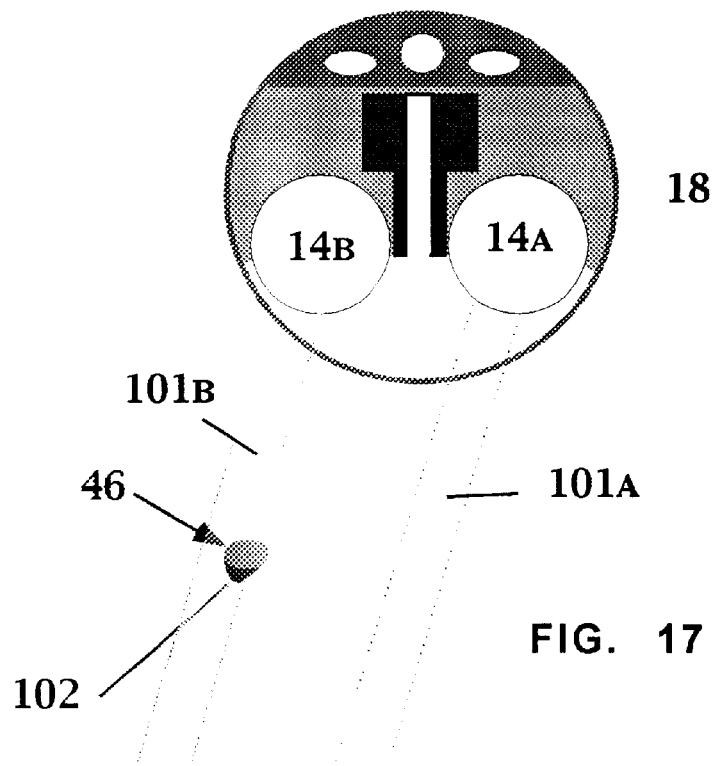
FIGS. 17 and 18 are sectional, schematic views showing the relationship of the dual beams emitted by the dual ultrasound scanners in the transrectal ultrasound probe. As the beams sweep across a tumor they cause different angles of acoustic shadow as shown.
Figure 18:
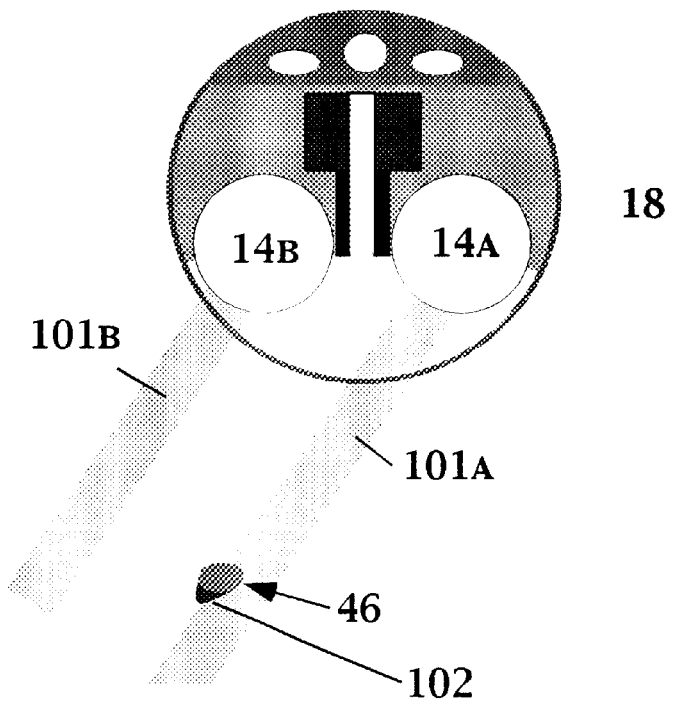

FIGS. 17 and 18 are sectional, schematic views showing the relationship of the dual beams 101a, b emitted by the dual ultrasound scanners 14a, b in said transrectal ultrasound probe. As the beams sweep across a tumor 46 they cause different angles of acoustic shadow 102 as shown.

FIGS. 19, 20, and 21 are sectional, schematic views showing three cross sections through said transrectal probe. FIG. 19 shows the custom silicon condum 81 which has a thickened back wall housing three lumens. The central lumen 88 is a passageway for a fiber optic viewer permitting visual inspection of the rectum during insertion of the transrectal probe. On either side of said lumen are two other lumens, one for filling the rectum with water 89 to act as a carrier for the ultrasound and one to act as an air bleed 90 for any entrapped air in the rectum. FIG. 20 shows the backbone 80 of the transrectal probe, flattened on the back to conform to the inside shape of said condum 81. The front is cutaway to form the cavity 19 housing the dual ultrasound scanners 14*a, b*. Between the ultrasound scanners is shown a cross section of the generator 91 for the dynamic elastography exciter. FIG. 21 shows the condum 81 in place surrounding and conforming to the backbone 80. The front of the condom 81 forms the outside wall of the cavity 19 housing the dual ultrasound scanners 14*a, b*.

Figure 22:
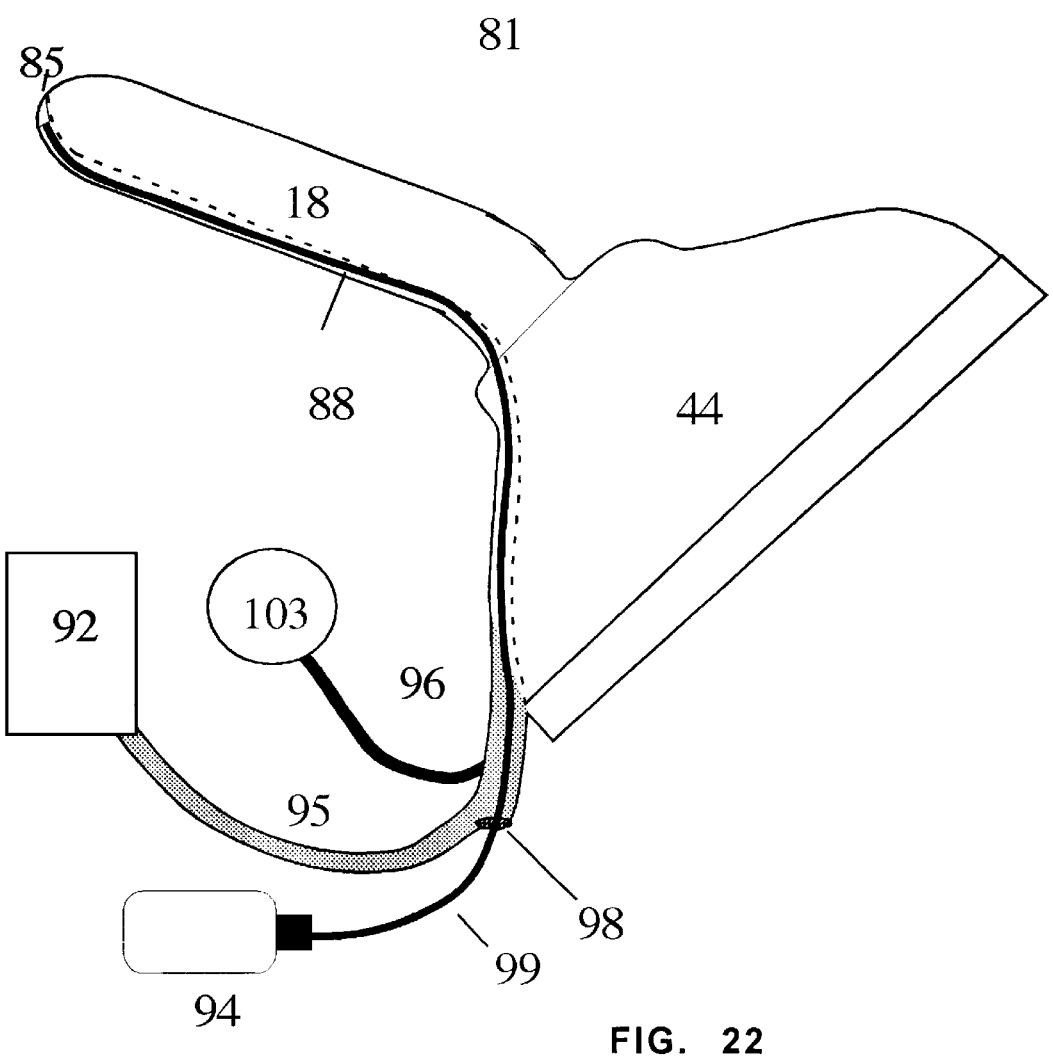
FIG. 22 is a sectional, schematic, view showing a side view of a condom covering the entire body of the transrectal probe.

FIG. 22 is a sectional, schematic view showing a side view of the condum 81 covering the entire body 44 of the transrectal probe. The aforementioned lumens continue down the back face of the body and are terminated in appended tubes 95*a, b* for inputting water, bleeding air and for the intromission of the fiber optic viewer 91, which passes into lumen 88 through a seal 98 terminated to a video camera 94.

Figure 23:
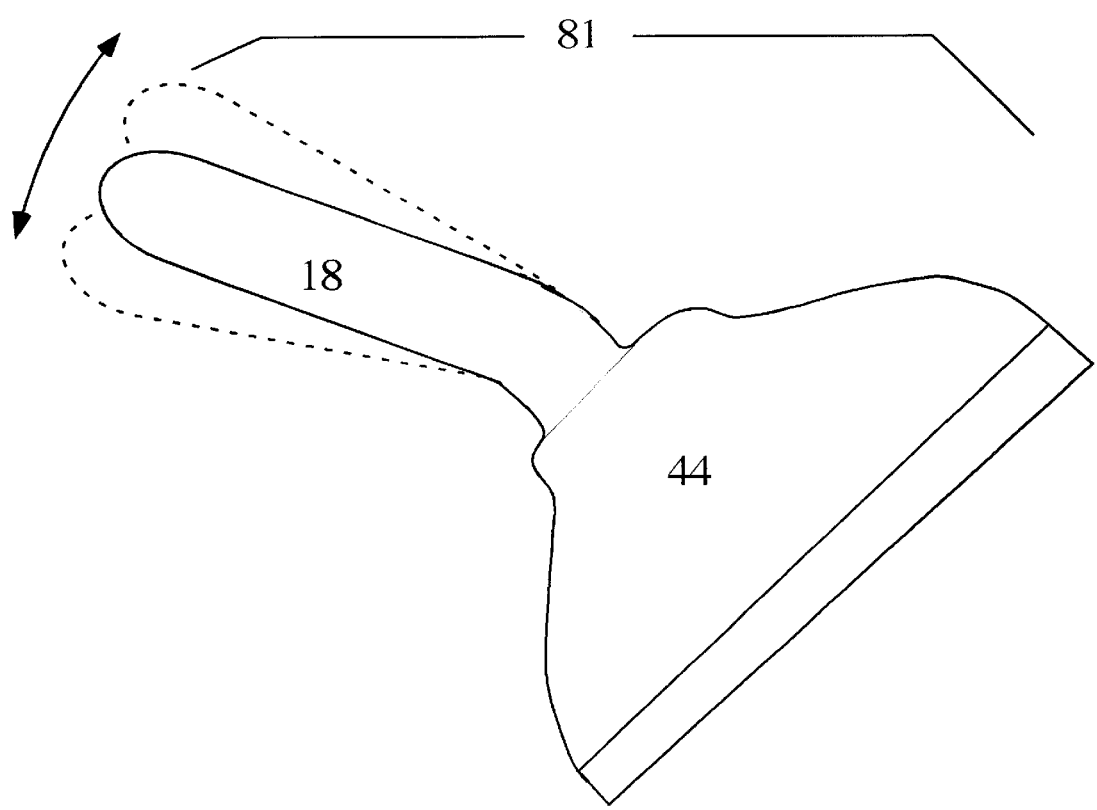
FIG. 23 is a sectional, schematic view illustrating that the transrectal probe body is flexible in the saggital plan in the region of the curved neck.

FIG. 23 is a sectional, schematic view illustrating that the transrectal probe body 44 at the junction with the probe tip 18 is flexible in the region of the curved neck in the sagittal plane.

Figure 24:
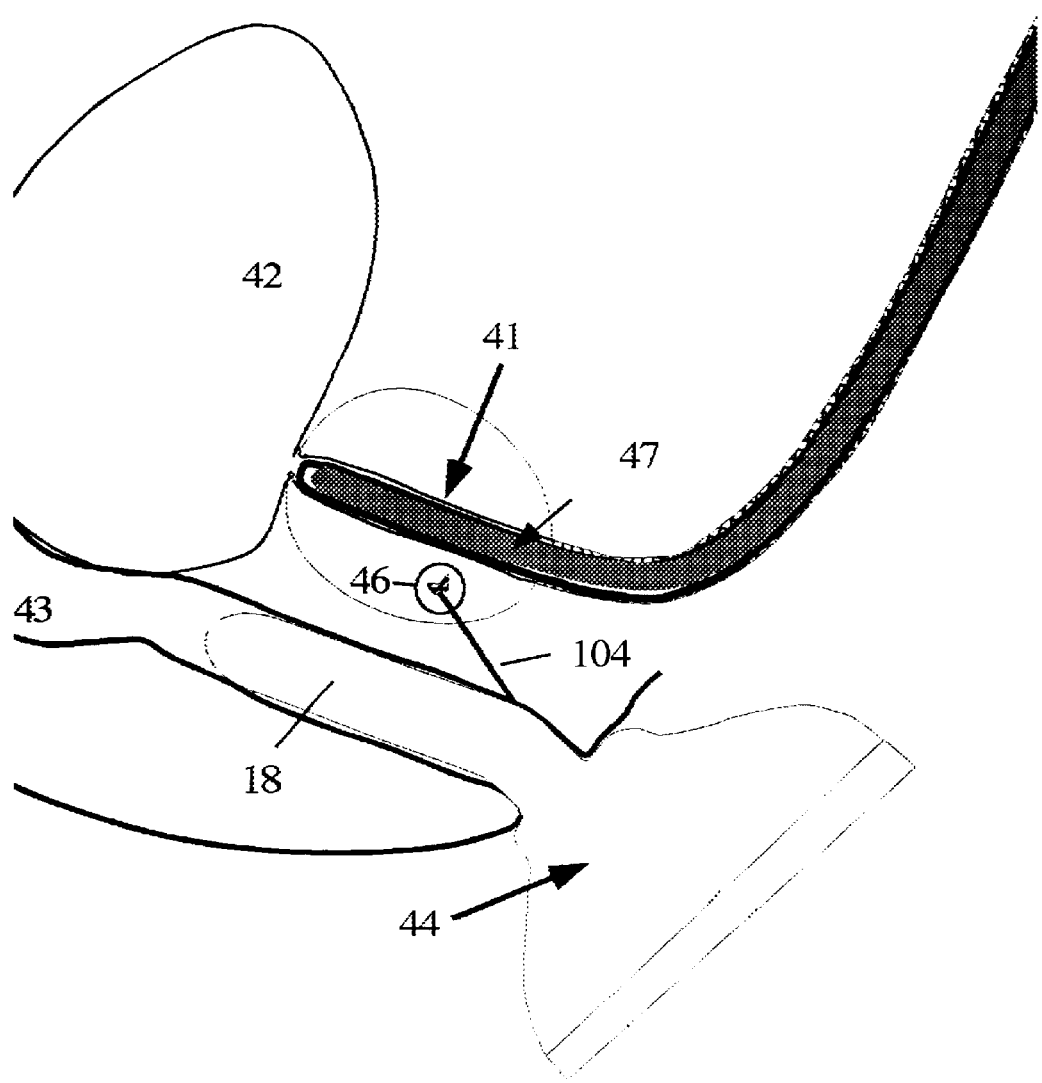
FIG. 24 is a sectional, schematic, anatomical view showing the transrectal probe body in situ within the body. The drawing illustrates that the slaved biopsy needle penetrates the condom when it is deployed.

FIG. 24 is a sectional, schematic, anatomical view showing the transrectal probe tip 18 in situ within the rectum 43. The drawing illustrates that the slaved biopsy needle 104 penetrates the condum 81 when it is deployed into tumor 46 within prostate 41.

Figure 25:
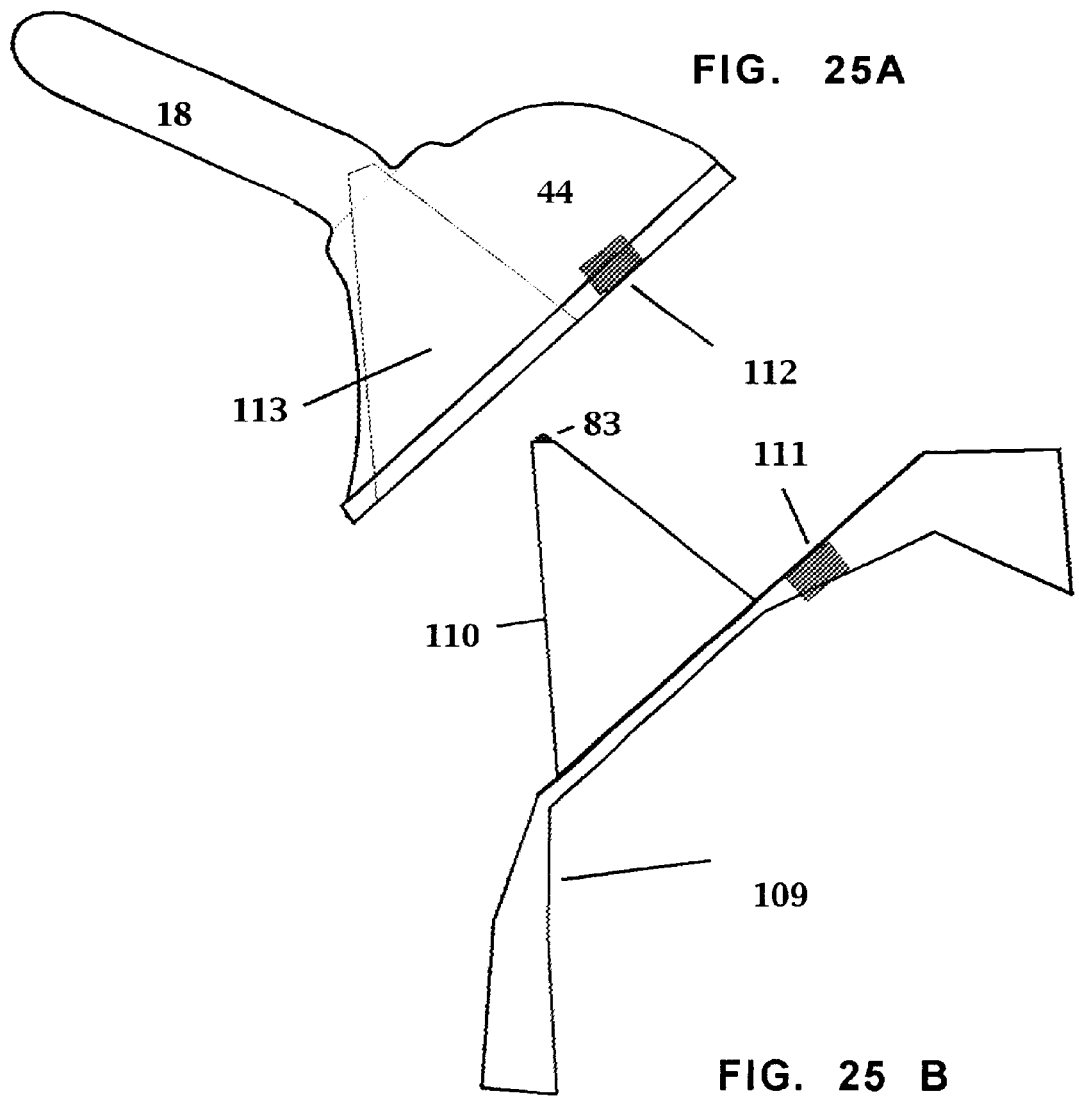
FIGS. 25A and 25B are sectional, schematic views showing the method by which the transrectal probe body is removably attached to the slaved biopsy needle mechanism housing. The non-symmetrical nesting inner and outer cone docking design guides the transrectal probe body to the proper position and alignment on the slaved biopsy needle mechanism housing and the magnetic latch holds it in place. These views show the elements before engagement.

FIGS. 25A and 25B are sectional, schematic views showing the method by which the transrectal probe body 44 is removably attached to the slaved biopsy needle mechanism housing. The non-symmetrical nesting inner 110 and outer cone 113 docking design guides the transrectal probe body 44 to the proper position and alignment on said slaved biopsy needle mechanism support structure 109, and the magnetic latch 111–112 holds it in place. These views show the elements before engagement.

Figure 26:
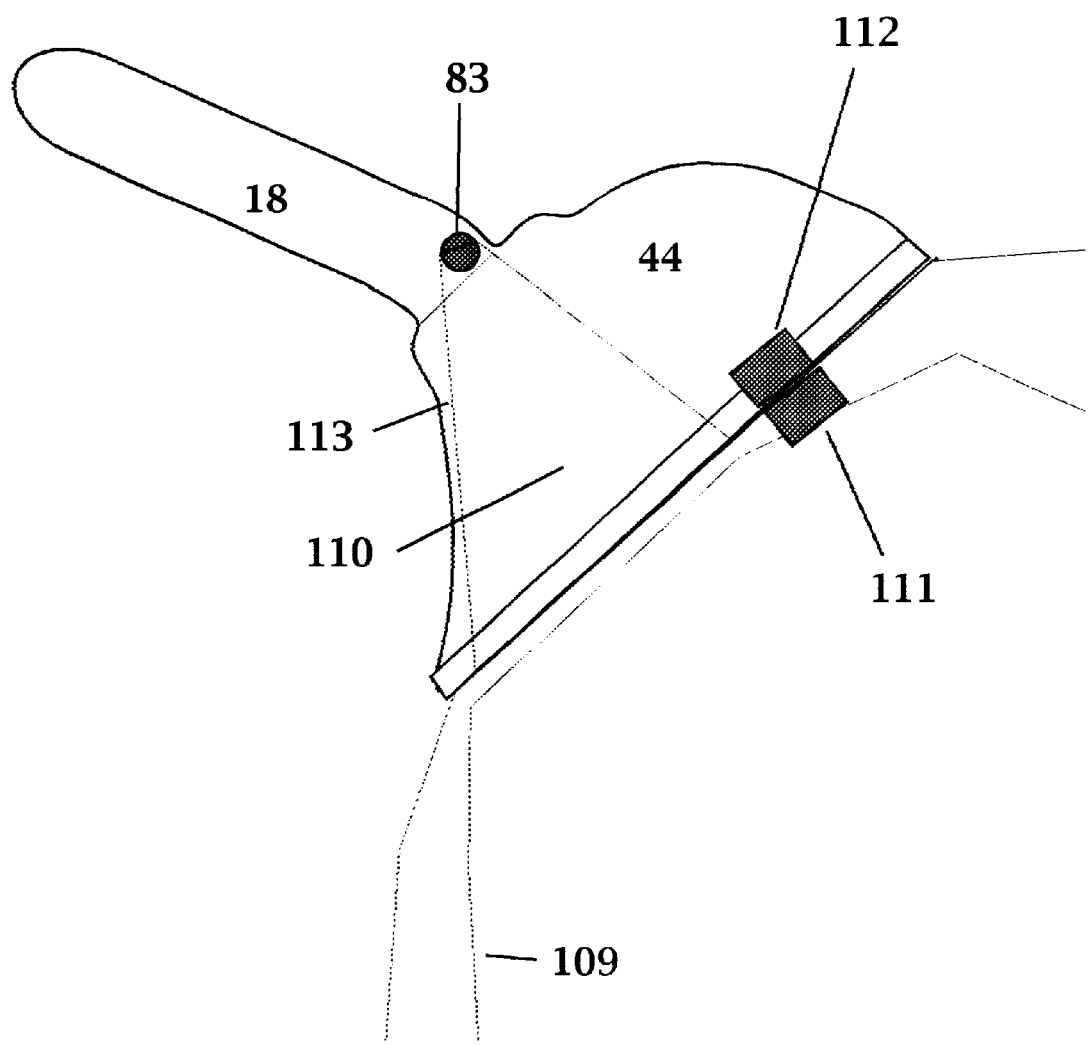
FIG. 26 is a sectional, schematic view showing the same elements as in FIGS. 25A and 25B after engagement is complete.

FIG. 26 a is a sectional, schematic view showing the same elements as in FIGS. 25A and 25B after engagement is complete, with cones 110 nested into cone 113 bringing gimbal 83 into the proper position inside the probe tip 18.

Figure 27:
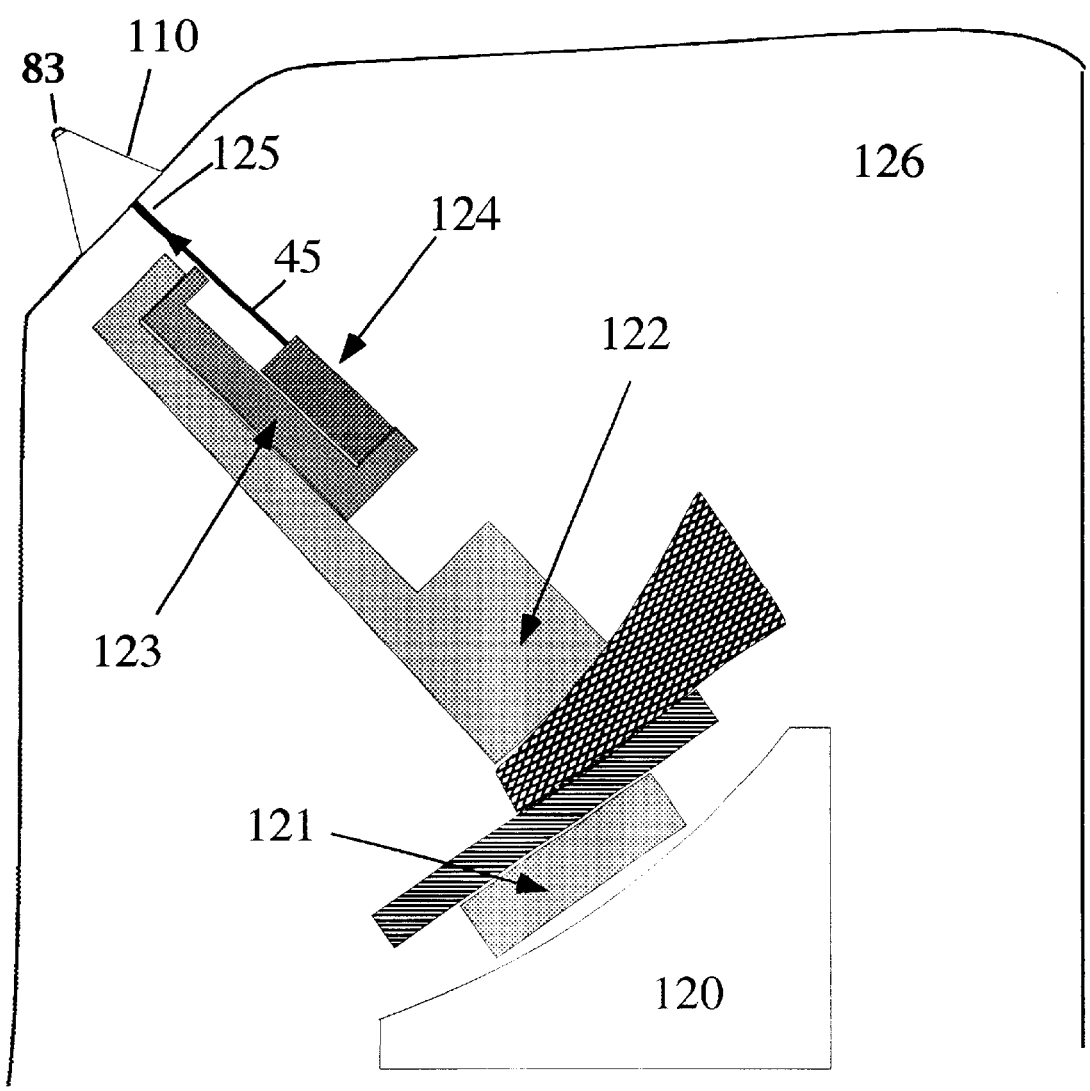
FIG. 27 is a sectional, schematic view showing the slaved biopsy mechanism within the housing. The drawing illustrates the relationship of the moving parts of the mechanism at the nominal rest position.

FIG. 27 is a sectional, schematic view showing the slaved biopsy mechanism within the housing. The drawing illustrates the relationship of the moving parts of said mechanism at the nominal rest position. 120 is the support structure, 121 is the rotary movement, 122 is the angular movement, 123 is the depth of penetration movement. 124 is the needle drive, 125 is the needle guide tube, which is suspended from gimbal 83, which is mounted to the tip of inner cone 110. The entire mechanism is housed within cover 126.

Figure 28:
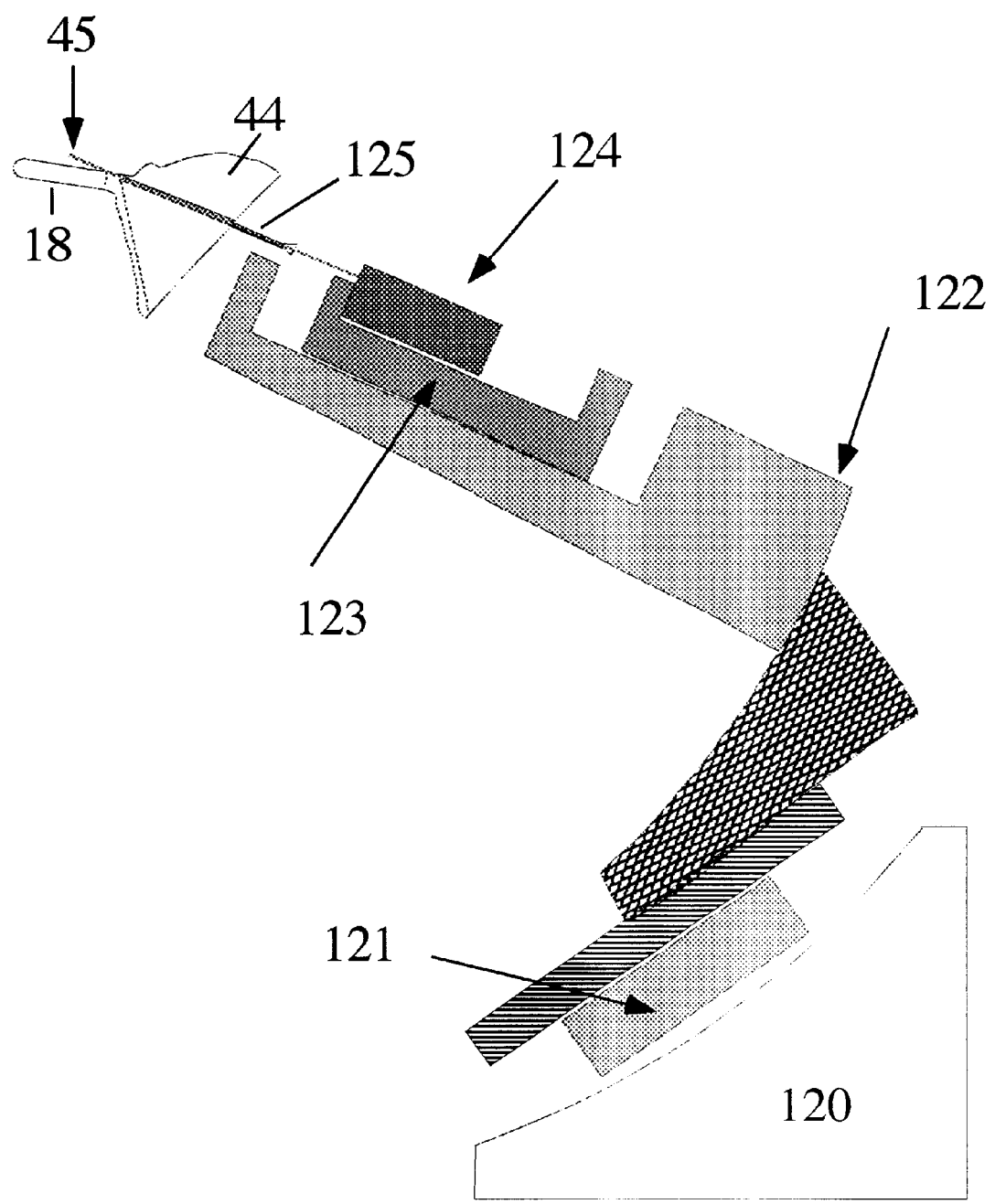
FIG. 28 is a sectional, schematic view showing the same elements as in FIG. 27 with the angular mechanism at the extreme of its travel.

FIG. 28 is a sectional, schematic view showing the same elements as in FIG. 27, with the angular mechanism 122 at the extreme of its travel.

Figure 29:
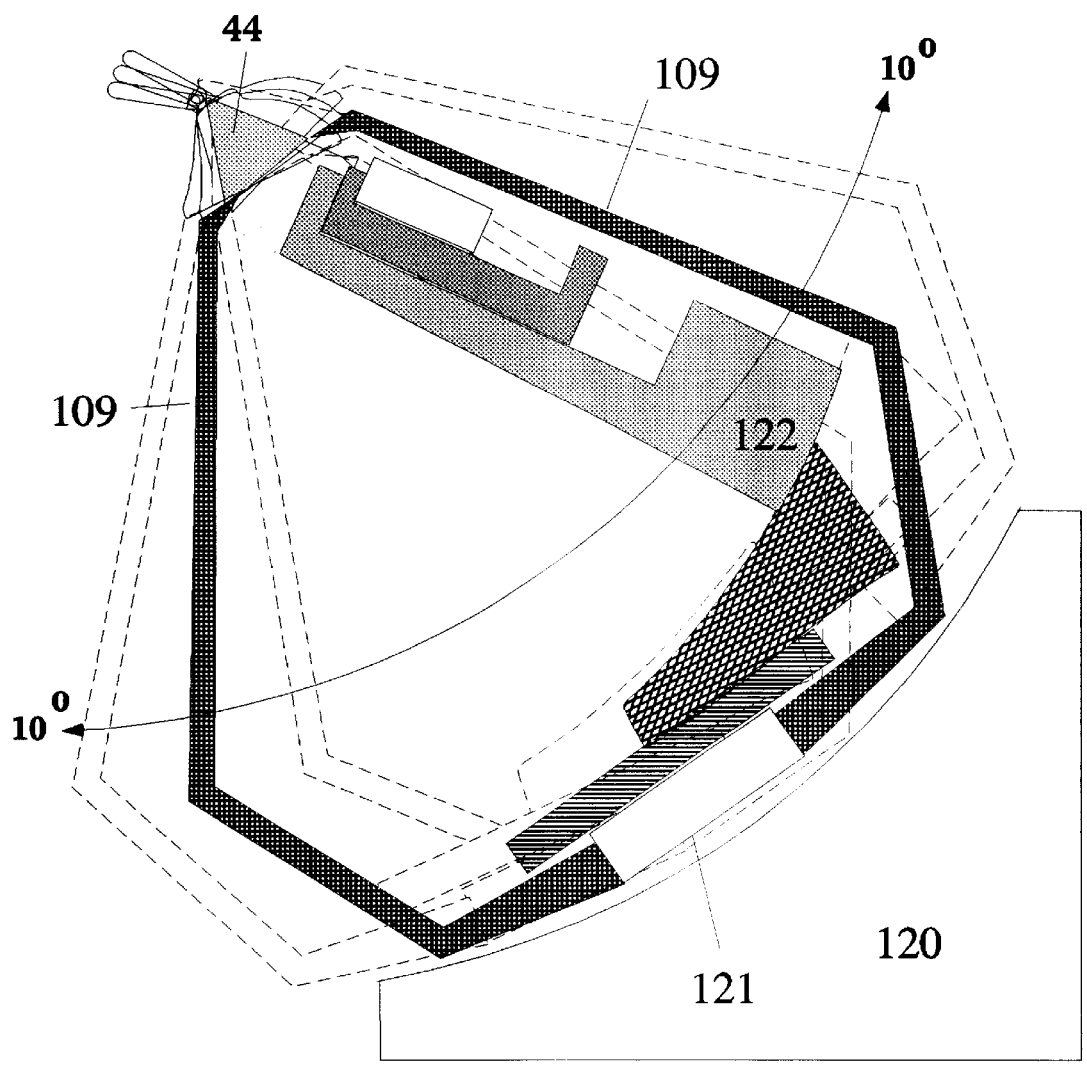
FIG. 29 is a sectional, schematic showing the same mechanism as in FIGS. 27 and 28 as it is carried within an angularly adjustable housing to facilitate optimal engagement with the patient regardless of anatomical variation.

FIG. 29 is a sectional, schematic showing the same mechanism as in FIGS. 27 and 28 as it is carried within an angularly adjustable cone support structure 109 to facilitate optimal engagement with the patient regardless of anatomical variation.

Figure 30:
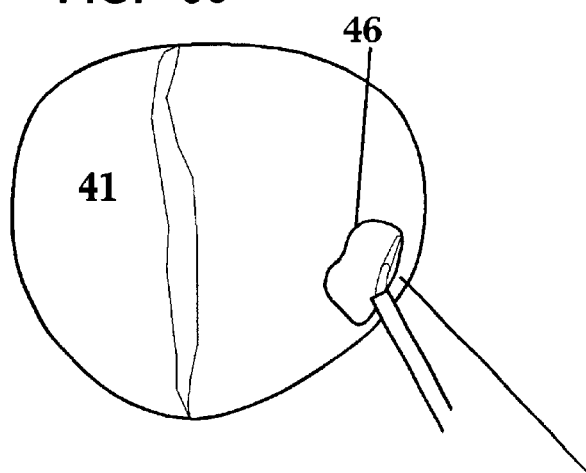
FIGS. 30, 31, 32, and 33 are sectional, schematic, anatomical views showing a sequence of the operation of a special tool which is deployed into a detected tumor.
Figure 31:
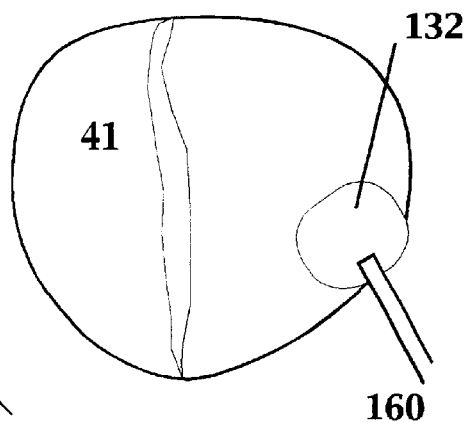
Figure 32:
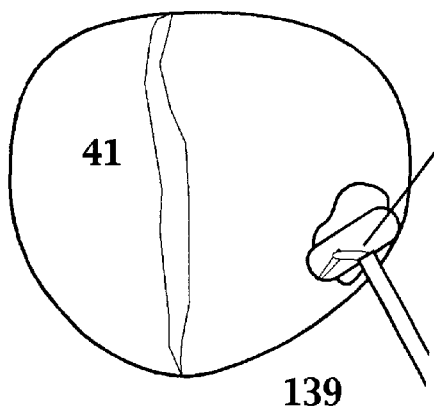
Figure 33:
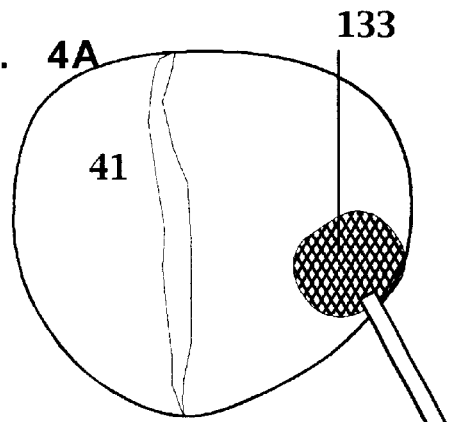
Figure 34:
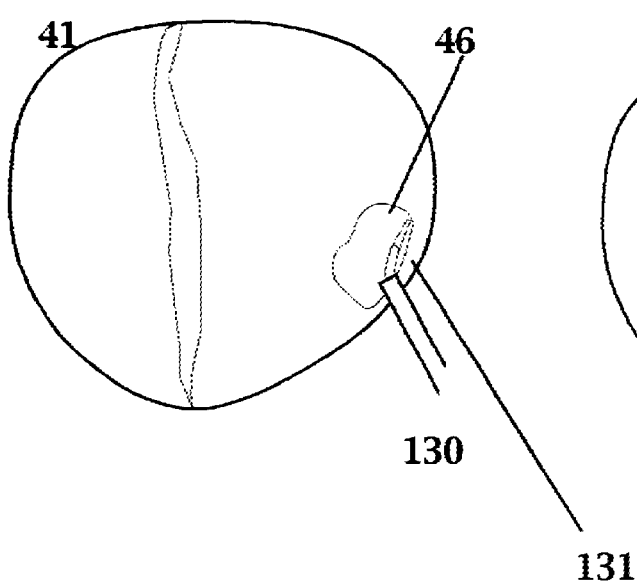
FIGS. 34, 35, 36 and 37 are sectional, schematic, anatomical views showing a similar set of sequences as in FIGS. 34–37. These drawings differ only in that instead of filling the cavity, a vacuum system is used to collapse the cavity. A tissue adhesive is then used to seal the opening.
Figure 35:
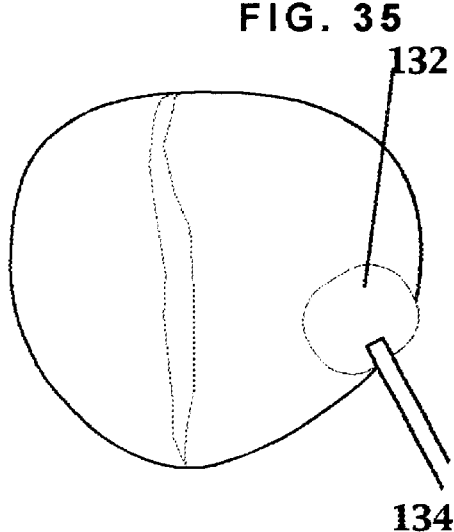
Figure 36:
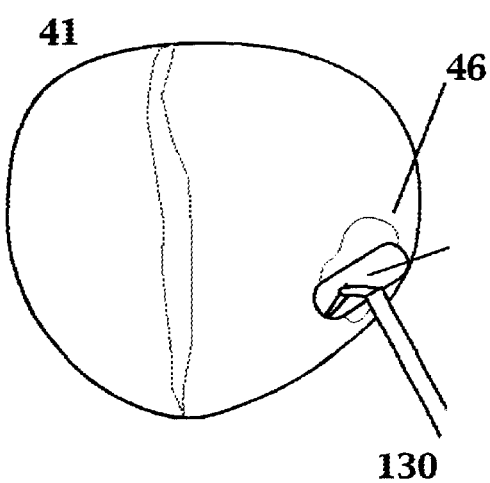
Figure 37:
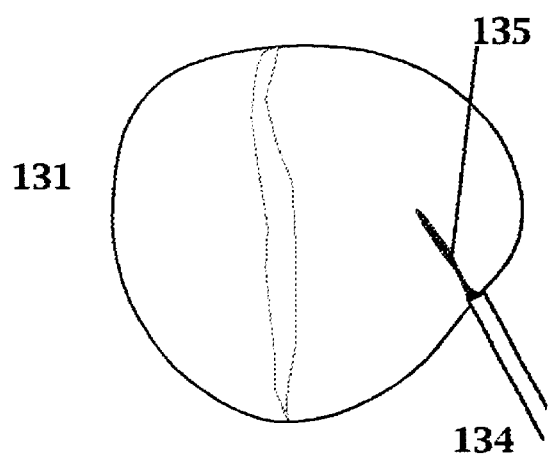

FIGS. 30, 31, 32 and 33 are sectional, schematic, anatomical views showing a sequence of the operation of a special tool which is deployed into a detected tumor. FIG. 30 shows a macerating needle and flail 130/131 deployed within tumor 46. FIG. 31 shows the tool reducing the volume containing the tumor to a liquid state. FIG. 32 shows the liquid extracted through the macerating needle 130 after removal of the macerating flail 131 leaving a cavity 132 where the tumor was. FIG. 33 shows the cavity filled with a collagen gel 133 derived from the patients own tissues and carrying the appropriate dosage of anti-cancer drugs.

FIGS. 34, 35, 36 and 37 are sectional, schematic, anatomical views showing a similar set of sequential views. The drawing differs only in that instead of filling the cavity, a vacuum working through needle 130, after removal of the flail, is used to collapse the cavity as shown at 135. A tissue adhesive is then used to seal the opening.

Figure 38:
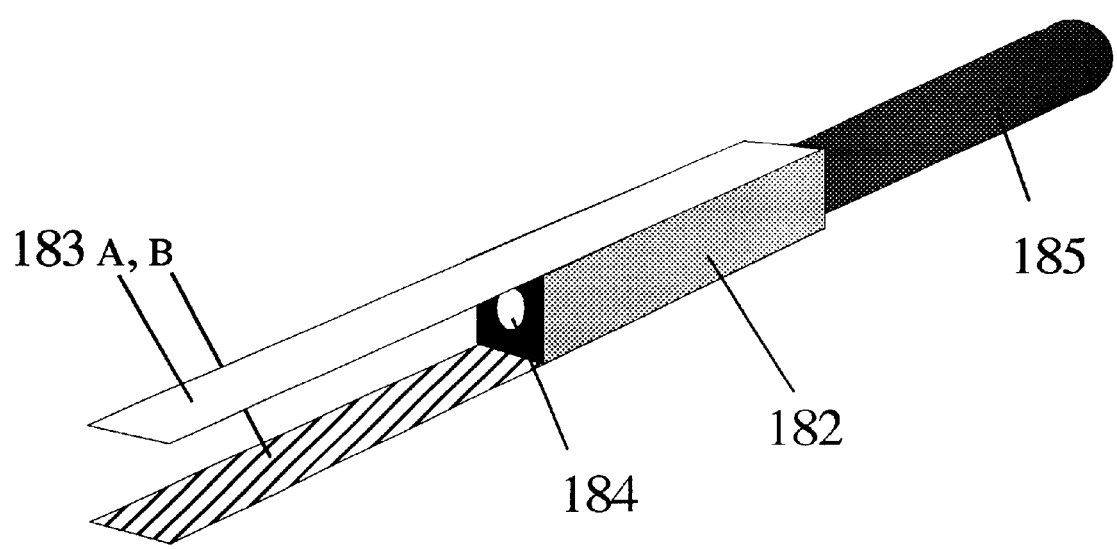
FIG. 38 is a perspective view showing the cutting mechanism of the slaved biopsy needle.
Figure 44:
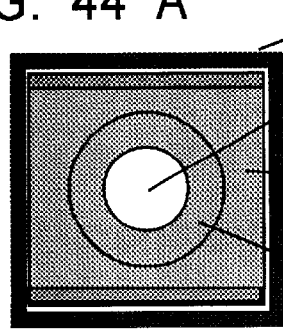
FIGS. 44A, 44B, 44C, and 44D are a set of drawings showing the square cross section of the needle and the fit of the cutting blades within the side plate guides.
Figure 44B:
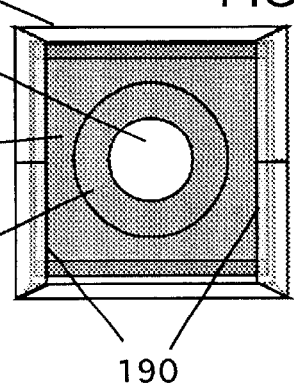
Figures 44, 44D:
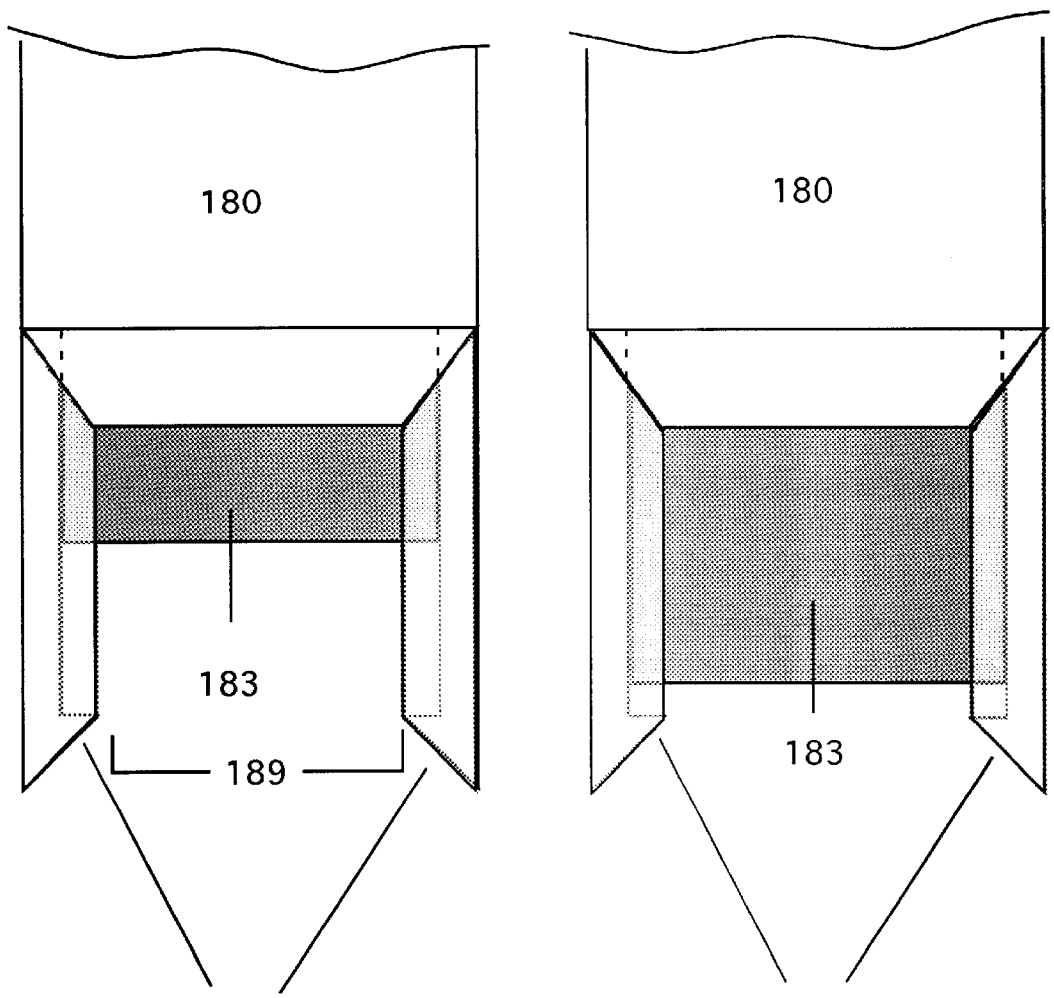

FIG. 38 shows the cutting element of the end harvesting biopsy needle. The cutting element consists of two thin square ended cutting blades permanently attached to opposite faces of a square slider element which is in turn mounted the end of a flexible push rod. Said push rod can be activated by any of a number of spring loaded, pneumatic, or electromagnetic mechanisms, which can be manually or automatically controlled. The slider element and the pushrod have a central lumen to relieve gas pressure from gas that could be trapped inside the needle when it is being forced into the tissue during the harvesting phase.

FIGS. 39, 40, and 41 show three cutaway views of the needle from the side. In FIG. 39 the cutting element is fully retracted leaving the mouth of the needle open. FIG. 40 shows the cutting element being advanced, with the cutting blades beginning to follow the curvature of the spear point side plate guides. FIG. 41 shows the blades advanced until they meet at the tip of the needle, separating and enclosing the harvested tissue for extraction.

FIGS. 42 and 43 are a set of drawings showing the square cross section of the needle and the configuration and fit of the guides with the cutting blades. FIG. 42 shows the cutting blades fully extended to cut off and enclose a tissue sample. FIG. 43 shows the open end of the needle during the harvesting phase of the biopsy.

FIGS. 44A, 44B, 44C, and 44D are a set of drawings showing the square cross section of the needle and the fit of the cutting blades within the side plate guides.

Figure 45:
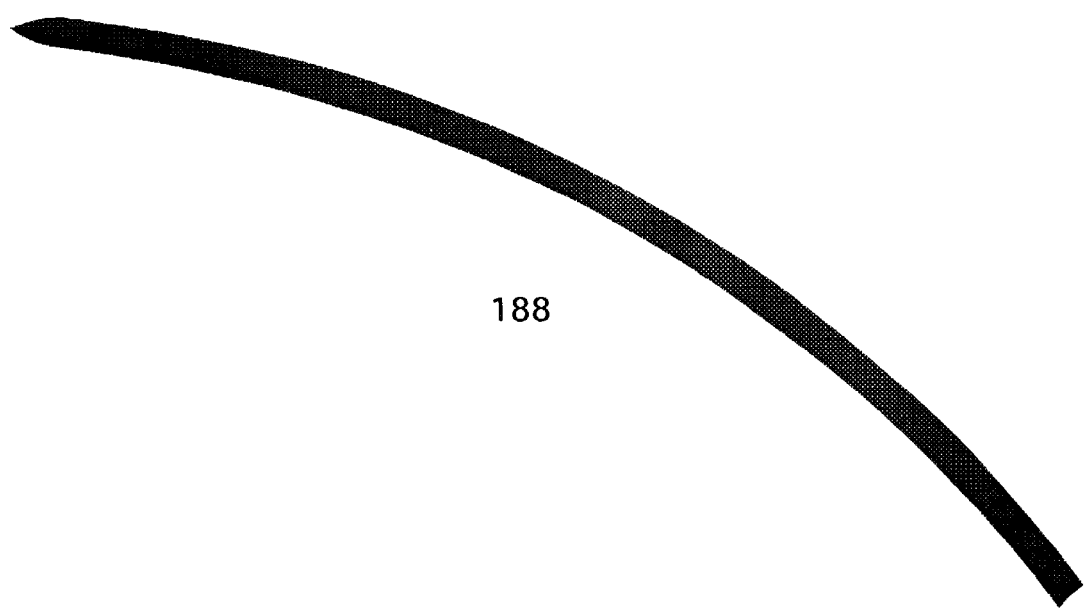
FIG. 45 is a perspective view of an alternate curved biopsy needle.

FIG. 45 shows an alternative curved needle with the same cutting mechanism for situations where such a shape would be desirable. Because the push rod is flexible, the degree of curvature is arbitrary and is tailored to the need.

Figure 46:
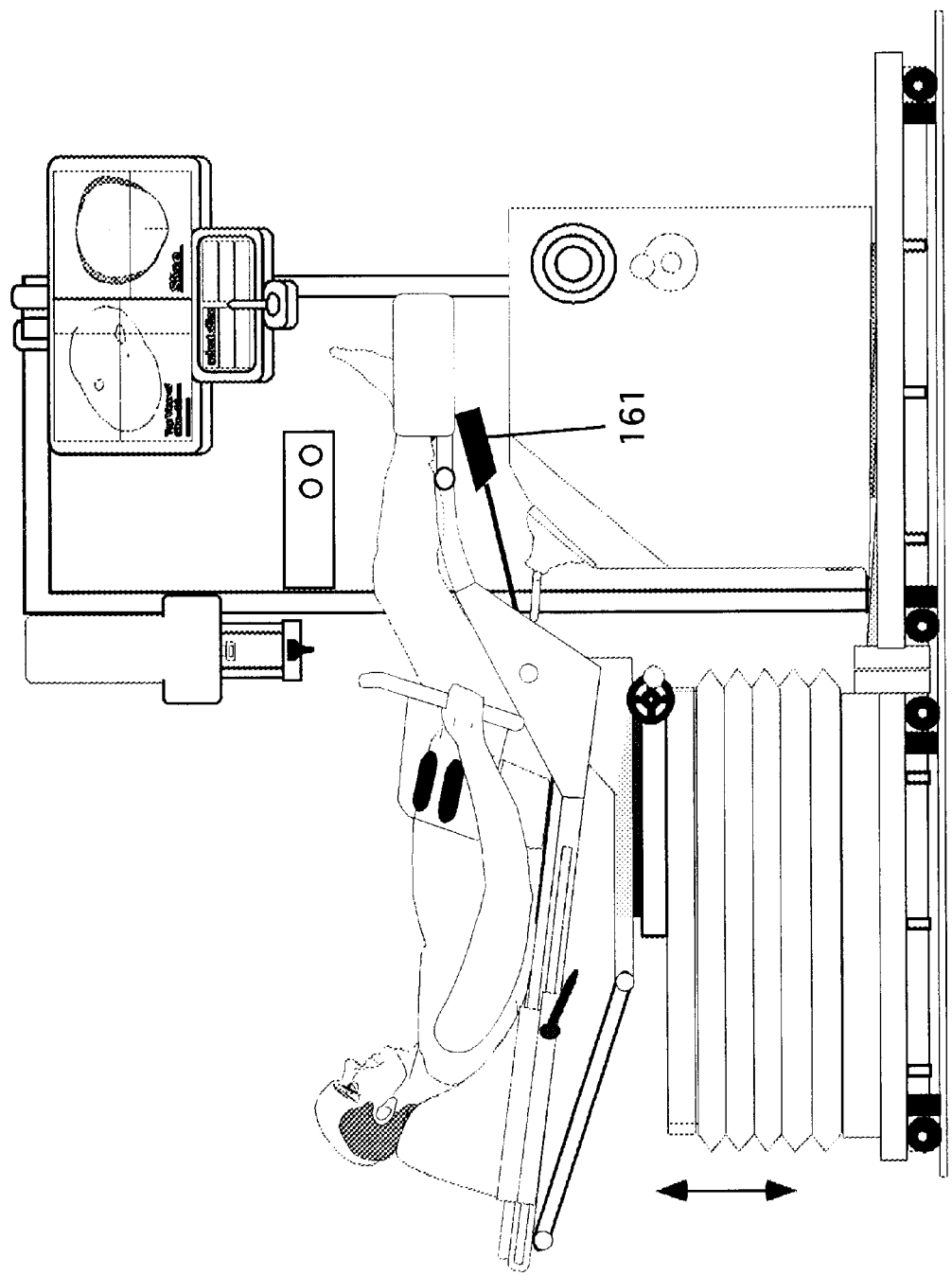
FIG. 46 is a sectional, schematic, anatomical view showing a patient in position of the integrated patient support platform.

FIG. 46 is a sectional, schematic view showing a patient in position on the integrated support platform. The drawing illustrates the use of a laser cross hair generator 161 to assist the doctor in positioning the patient's anus at the proper point in space for correct alignment of all of the complimentary system elements.

A detailed description of the making and using of the instant system follows. The patient is reclined on a powered, adjustable chair at an angle between 0 and 20 degrees up from the horizontal, depending on the anatomical requirements of the individual for the comfortable placement of the dual diagnostic probes. This adjustment is under the full control of the doctor. The chair itself rotates and lowers for ease of patient entry. After the patient is seated the chair elevates and rotates to align the patient on centerline and reclines to the angle selected by the doctor. A laser cross hair provides a reference point in 3D space for the optimal initial positioning of the patient. The final positioning of the patient is recorded in the data file for the procedure, so that any subsequent examination can be returned to the same alignment to ensure repeatability. Additional functional elements mounted to the chair include, but are not necessarily limited to: sub-elements of the magnetic position sensor used to track and record the absolute position of the transrectal probe. The ventral set of driver elements for the dynamic elastography analysis augmentation sub-system. Various baseline physiological monitors are incorporated into the chair cushions to simplify the monitoring of patient status.

The dual diagnostic probes are the transurethral and the transrectal. The description and usage is as follows: Interaction with the doctors has lead to a definition of the relationship and procedures for the use of said probes. The transurethral subsystem consists of several elements. The ultrasound sensor drive system, which has a linear drive, a rotational drive and a signal/power/mechanical connector, is mounted on a movable structure above the area of the patient's groin. This facilitates the introduction of the transurethral probe with the penis in essentially a vertical position, as is commonly done for the introduction of other types of catheters. The drive system can be slidably moved in the vertical plane for adjustment to anatomical patient variability. It can also be slidably moved away from the patient for working clearance during other parts of the procedure. Towards the distal tip of the transurethral drive vertical movement is the signal/power/mechanical connector for the ultrasound diagnostic probe. At the distal tip of the vertical movement is the receptacle into which is inserted the catheter feeder which forms the upper end of the transurethral catheter. This serves the twofold purpose of maintaining the proper relationship between the top of the catheter and the transurethral drive for connecting the ultrasound diagnostic probe, and it also serves to hold the relationship between the catheter and the patient after the catheter/fiberscope combination has been inserted into the correct position within the patient's prostate. The transurethral catheter is 12–14 French in diameter and of a length to suit the individual patient. The catheter is inserted by the doctor through the penis, the prostate and into the bladder using a coaxially contained, articulated fiber optic scope as a guide. At the beginning of the procedure, said articulated fiber optic is threaded through the length of the catheter, such that the articulated portion protrudes through a small opening in the distal end of the catheter. A flow of water is introduced into the lumen of the catheter via the catheter feeder device to which the proximal end of the catheter is attached. The catheter and catheter feeder are permanently connected and supplied as a single unit. The catheter feeder performs a number of functions. The catheter feeder consists of a plastic block with a passageway from top to bottom. In a recessed gallery at the top of the passageway there is a soft, silicone rubber O-ring through which the fiber optic and diagnostic probes are inserted so that they go through the passageway and into the catheter. The O-ring forms a seal to insure that the water, which is introduced into the passageway via a side port, flows down through the passageway and into the catheter that is attached to the bottom of the catheter feeder by a spigot fitting. The water flows around the fiber optic and out through the tip opening around the shaft of the fiber optic. This forms a bolus of water ahead of the catheter as it is advanced through the urethra. The bolus serves both to open the urethra for the passage of the fiber optic guide and the catheter and to lubricate the interior of the urethra. Said water flow also may carry a topical anesthetic to reduce any patient discomfort during the procedure. Said water is introduced under a low pressure via the leuer fitting mounted on the side port of the catheter feeder. The distal end of the catheter may have additional openings to ensure a completely wetted outer surface. The physician uses a viewing screen to guide the fiber optic, via the articulation, through the urethra, into the bladder. The interior of the urethra, the prostate and the bladder can be viewed in this manner, while at the same time the fiber optic shaft acts as a coaxial guide wire for the catheter. After optical examination of the bladder, the fiber optic is withdrawn to a point just within the upper sphincter of the prostate. The distal tip of the catheter is now advanced to be coincident with the fiber optic tip, thus placing it in the correct relationship to the prostate for the diagnostic scan procedure. The vertical movement of the ultrasound drive mechanism is now unlatched and manually moved down to a point immediately adjacent to the catheter feeder block, where it is reached into immobility. Said catheter feeder block is fitted with a rearward projecting latching mechanism, which is now inserted into the distal receptacle, thus holding the correct relationship between the patient and the transurethral ultrasound drive mechanism for the remainder of the procedure. At this time the fiber optic is withdrawn completely from the lumen of the catheter through the catheter feeder. Water continues to flow into the lumen of the catheter as the fiber optic is withdrawn, via the side port of the catheter feeder. This leaves the lumen filled with water for the insertion of the ultrasonic diagnostic probe.

The Physician now inserts the ultrasound (or other desired modality) examination probe through the upper port of the catheter feeder. The distal end of the examination probe is advanced until it reaches the distal end of the catheter which is already in place. The tip opening that allowed the passage of the fiber optic is smaller than the diagnostic probe, so that the end of the catheter stops the forward movement of the diagnostic probe at the right place. The water eases the movement of the examination probe and the amount that is forced out of the tip opening will fill the prostatic urethra so that an inserted ultrasonic examination transducer assembly can operate in a water bath that fills the lumen of organ. The intent is to give optimal ultrasonic transmission into the volume of the prostate.

A second diagnostic probe is introduced transrectally. Said probe is flexibly mounted to better accommodate minor anatomical variations between patients. Said probe contains passageways within the probe cover to flood the rectum with water, again for optimal ultrasonic transmission. A second passageway serves to bleed off any displaced air as the rectum is filled with water. Said probe also contains a second optical system which is resident within a third passageway in the probe cover, giving a wide field of view in front of the distal end of the probe. The interior of the rectum can thus be examined for abnormalities during the insertion period of residence and removal of the probe from the body.

A preferred embodiment of the transrectal probe is described as follows: instead of a single oscillating ultrasonic transducer head which steps vertically through the rectum, the transrectal probe is mechanically modified to accommodate two scanning head assemblies. The two assemblies are identical in size and structure, and are mounted such that they view the area of the prostate in parallel with some separation between them. Mechanically these two assemblies are linked in such a manner that they step along the longitudinal axis together. Further, the driving electronics can pulse and/or receive from each assembly simultaneously or in sequence, providing a further means for shadow analysis in the overall diagnostic capabilities. Such an arrangement can accommodate phased arrays or each assembly can operate at different frequencies to increase the potential capability of the system.

A second alternative embodiment of the transrectal probe is optimized for patient comfort in cases where there is not an expectation of a requirement for a biopsy. In these circumstances a self-contained transrectal probe does not require the enlarged neck of the biopsy probe, therefore only a small cable passes through the anus for the dual purposes of extracting the data gathering probe and for carrying the electrical and data signals to and from the control apparatus.

Functionally, said probe serves the same diagnostic purpose as the previously described transrectal probe. It differs only in that the location and angle of the probe is determined and recorded by a magnetic positioning system. Said free floating system has the virtues of a) minimal distention of the anus during the examination (the primary source of discomfort to the patient associated with the transrectal examination.) and b) essentially infinite flexibility to accommodate itself to variations in the rectal anatomy and angle between patients. At the same time it provides recorded information on the exact positioning of the probe within the rectum, such that should the patient require a rescan, and/or a biopsy at a later time, the second probe insertion can be to the same spatial coordinates and angle as the first for repeatability.

The two ultrasound scanners (transrectal and transurethral) move axially through the volume of space containing the prostate in sequential steps numbered from the point of origin at one end of the mechanical movements to the hard stop at the other end of the movement. Each step corresponds to a scan slice. The ultrasonic data is acquired as a series of tomographic type slices, each of which is approximately 1–2 mm thick.

The software assembles the acquired slice data into a 3-dimensional image stack for volumetric analysis and then presentation to the doctor as a level of suspicion map of the patient's prostate. The location in space of any suspect area is determined by the computer and displayed to the physician. The numbered slice in which it occurs defines the axial location of each detected structure.

In order to improve speed of actuation, mechanical robustness, safety and patient comfort, the biopsy needle uses an offset biopsy system which computes the geometric relationship between the scanning systems and the designated biopsy target.

Said offset mechanism permits the use of mechanical movements similar to those used in high precision machine tools for aiming control. Said offset mechanism also permits the use of a pneumatically driven biopsy needle activation system which will fire the biopsy needle exactly to the physician designated point, take the biopsy sample and then extract the needle very rapidly for minimum patient trauma. A side benefit to the high speed of the pneumatic system is that the inertia of the tissue into which it is being fired will tend to lessen the possibility of the needle penetration of the prostate displacing the organ, which can push the target area out of alignment.

Said offset mechanism also permits the easy removal and replacement of the biopsy needle and the contained sample. An improved biopsy needle has been designed to further enhance the capability of the system. Conventional biopsy needles use a beveled tip and take the tissue sample by shearing the tissue on the long axis of the sample. Both of these design features have undesirable side effects. The beveled tip can cause the needle to deflect to the side ("plane") as it passes through the tissue, particularly if the path of the needle happens to intersect a denser tissue area at an angle. An additional deficiency of current biopsy needles is that the longitudinal shearing action of their sample gathering mechanism can produce more tissue distortion than the pathologists would like to see, thereby making diagnosis more difficult. If the tissue is too dense the current design will sometimes not retrieve a tissue sample. The improved needle design has a square section, bilaterally symmetrical "javelin" point, which has little or no tendency to deviate from the desired path. It is an end harvesting design that cuts and encloses the tissue sample via to two opposing cutting blades that "nip" off the tissue sample. Such an arrangement produces less distortion of the tissue for more accurate examination and analysis by the pathologist.

As a safety feature, when the physician has selected the biopsy site, the computer will set the X and Y needle guide movements to the correct position and then will set the Z movement to control the depth of penetration. The boundaries of the prostate are shown on screen along with the slice number and computed location of the point to be biopsied.

For further safety consideration an independent sensor mounted on each axis of the movement verifies the actual position that the mechanical movements have taken in response to the computer command. That position will be displayed on screen and should agree with the computed slice number. The physician makes that comparison and if satisfied with the concordance he activates the "Biopsy Armed" control. Only when this step has been accomplished does the computer give access to the "Activate Biopsy Needle" command box. This functionality is not disclosed by any other biopsy system.

An alternative method of determining if a detected, suspicious area is in fact malignant is disclosed herein. A miniature coil, mounted on the transurethral probe is used to impose a pulsating field on the volume of the prostate. This field is detected by a complimentary coil mounted on a specially modified biopsy needle. The sensitivity of the sensing coil is modulated by the bioimpedance of the tissue immediately surrounding the tip of said biopsy needle, i.e. the area of suspicion into which it has been directed. Studies have shown that the bioimpedance of a malignant cancer differs markedly from that of a benign tumor, or from normal tissue. This data can be used to corroborate, or to give a quick indication of the threat posed by that area of suspicion. This technique appears to offer advantages over the laser florescent technique that has been reported in the literature, since it works over a volume of tissue and does not require the direct exposure necessary for laser florescence. An alternative embodiment would use two coils mounted directly on the biopsy needle. Such an arrangement would give a more localized reading. The physician interacts with the computer via sealed, sterilizable touch controls. He or she uses a touch pad to select the target of interest for biopsy by sliding the intersection of a set of full screen cross hairs to the center of the desired area and touching the select button.

Most of the controls take the form of a series of nested menus of on screen dialog boxes. The control menus are hierarchical with only a small number of context sensitive controls on screen at any one time. There is a full time, context sensitive help window that defines the functionality of whatever control is currently selected. For activities where it is appropriate for safety reasons, the help window will be supplemented with a prerequisite check list, each element of which must be checked off by the physician before the next one is displayed. All check list elements must be cleared before the command functionality is enabled.

A special chair is incorporated for maximum flexibility and accuracy in the positioning of the patient for these and other urological procedures. The chair is designed for ease of patient entry and exit. It quickly adapts to the size of the individual patient for comfort, and has multiple degrees of freedom for positioning of the patient. The system incorporates a laser cross-hair alignment system to assist the physician in moving the patient so that the patient's anus is in the optimal position for insertion of the transrectal sensor probe.

The transrectal probe uses dual side scanning ultrasound systems. The upper portion of the probe comprises the scanning transducer capsule and is less than 1 inch in diameter and less than 4 inches long, having a conical, rounded tip. In use the exterior surface is completely covered by a disposable cover. The cover is made from a material which has prior FDA approval. The scanning transducer capsule houses the scanning transducer systems which move longitudinally through the capsule in parallel. The transducer heads move along the longitudinal axis in a series of steps of about 2 mm. Each step corresponds to a sequentially numbered data slice taken transversely through the prostate. At each step both transducer heads would scan through the volume containing the prostate. The result is a series of broad, thin, scans into the prostate which overlap the complimentary scans being performed by the coordinated second system operating within the urethra. The overall effect is that of electronically dissecting the prostate into a large number of thin slices. Those slices are then integrated and analyzed by the expert system software and a level of suspicion map is presented to the doctor. Additionally, if desired, those slices can then be examined and manipulated by the physician in the virtual space provided by the computer. A second alternative transrectal sensor arrangement is to separate the transmitting and receiving functions to different types of transducers for the purpose of optimizing their respective functions.

The transrectal scanning transducer biopsy capsule is mounted on a hinge joint so that it has a controllable fore-aft movement range in the sagittal plane to accommodate patient anatomic variability. A magnetic locating system is provided to give the precise location and relationship of the transurethral and transrectal probes, for data correlation.

Below the base of the sensor capsule, the remainder of the transrectal probe consists of a curved neck, which passes through the anus. The sensor capsule is mounted to the top of a handpiece, which is held by the physician if manual insertion is desired. The handpiece terminates at the top in a rounded bulge which serves as a stop to prevent it from being inserted too far into the rectum. The lower end of the handpiece couples, and is latched to the top of the canister that houses the slaved biopsy mechanism. The outer surface of the neck is covered by a continuation of the covering of the sensor capsule that acts as a seal to retain the water that has been injected into the rectum to provide an optimum ultrasonic environment, as well as accommodating the flex of the nodding movement.

The neck of the transrectal probe removably encloses the gimbal needle exit that is the pivot point for the aforementioned offset biopsy mechanism. The offset biopsy mechanism consists of the following parts:

The spherical gimbal for the biopsy mechanism is mounted in a socket at the top of a hollow, cone shaped support structure. The exit of the needle guide tube passes through the center of the spherical gimbal. The needle tube hangs from the gimbal down through the cone, which gives it complete freedom to be moved to any angle within the boundary of the cone. The upper end of the tube is flush with the surface of the sphere, while the lower end protrudes downwards and functions as a coupler between the gimbal and the remainder of the slaved biopsy mechanism.

Said gimbal is mounted at the tip of a supporting cone that is permanently mounted to the tip of the canister that houses the X, Y, Z biopsy needle positioning mechanism and the biopsy activation mechanism.

When the transrectal probe handpiece is placed on the top of the said canister, said gimbal and cone pass into and are seated into a close fitting conical socket internal to the transrectal probe handpiece.

When the transrectal probe handpiece is seated onto said support cone, it locks into place. When the locking action takes place, the gimbal cone fills the internal socket of the transrectal handpiece and fixes the geometric relationship between the slaved biopsy exit point and the transrectal sensor movement thus providing known coordinate inputs for the system software. Just below and adjacent to the point at which the needle will exit through the probe cover, said cover is provided with an inflatable ridge which serves to push any adjacent anal tissue down and away from the space through which the biopsy needle will be fired. Outside of the cone socket, the wall of the cover neck houses a number of lumens which lie along the slope of the outer cone, and through which pass the various mechanical elements which actuate the movement of the scanner. Ducts that provide for removal of any gas present in the rectum and the introduction of the ultrasonic water medium, and the deployment of a fiber optic system for the examination of the interior of the rectum are provided in the thickened back wall of the disposable probe cover. Since the feed tubes for water are extensions of the disposable cover; they are also disposable for the sake of cleanliness between patients. The concept of incorporating passageways into a modified condom-type cover for the probe rather than having them internal isolates the interior of the diagnostic probe and greatly simplifies the process of cleaning and sterilization.

As an enhancement to the overall system in order to increase the sensitivity of the mapping, analysis and detection systems, the capability of performing an acoustic/ultrasonic technique called Dynamic Elastography is added as a sub-system to the set of available diagnostic techniques available in the present system. This embodiment differs from previous examples of the technique in that it uses a far more sophisticated method of excitation. Other implementations of the technique have used: focused ultrasound shear waves, mechanical cam type tissue displacement, or acoustic voice coil type exciters. All of the above use uniaxial presentation and a limited frequency and power capability.

In the present invention, the intent is to provide higher coercive force, a broader excitation spectrum, and the capability for the selection of different angles of excitation presentation. The result is to provide a high available power, tunable excitation, where the angle of presentation to the prostate can be varied to excite different stiffness modes within the prostate, thereby enhancing the positive effects of dynamic elastography on the data acquisition from, and analysis of, any existing pathology within the prostate. The excitation elements are based on piezo-electric material. Piezo-electric materials produce a higher coercive force than other types of acoustic generators and are therefore, perfectly suited and give more capability than any previous technique for dynamic elastography. One set of transducers are applied externally to the lower abdomen. The transducers are housed in an adjustable belt like arrangement. A second set of transducers are mounted on slidably "hip fences" which are adjusted to snugly fit against the patient's hips, which are incorporated into the specially designed chair of the present system. A third set of transducers are below the patient's lower back. A fourth set of transducers are embedded in the surface of the transrectal probe, above and below the window through which the diagnostic ultrasound scans the prostate interior. By using combinations of these transducer groups, excitation waves can be produced in the prostate from many different directions. This means that any available mode of vibration within the prostate can be excited, with positive impact on the identification, location, and diagnosis of any pathologic conditions existing within the prostate. These transducers impose a modulated, frequency swept, sound wave to the abdomen, which causes a vibration of the internal structures, including the prostate. Because vibration interacts most strongly with the viscoelastic properties of various tissues, this technique will cause areas of different "stiffness" to vibrate differentially. The movement pattern is then detected by pulse-echo doppler ultrasound interrogation contained in the present system. This technique has the potential to enhance and make visible prostate cancers that would not normally be detectable owing to small size or lack of distinguishing characteristics in normal grey-scale imaging. A further enhancement to the system is the inclusion of the ability to do doppler blood flow measurements over time (4-D).

Because of the coherent archiving of the patient data all measurements and scans can be accurately repeated at time intervals, and automatic digital correlation is used to produce a time-variation history for each detected condition which tracks, and quantifies the progression of the condition, a further aspect of the expert system.

A further enhancement to the present slaved biopsy subsystem is the inclusion of a treatment system which is appropriate for intervention in the case of small, detected and confirmed cancers. A special biopsy needle is available which can be fired into the detected cancer and will stop in place within the cancer. The embedded tip of the needle contains a heating element that can elevate the temperature of the surrounding tissue to above the 43 degree C. temperature; which will kill the cancer cells. Because the necrotized tissue produces a different ultrasonic return than living tissue, the area of killed tissue can be monitored real time to verify that the volume of killed tissue is larger than the previously mapped volume of the detected cancer. Archiving of this data would also permit tracking the condition over time to verify that all of the cancer was indeed killed.

A further enhancement of the present slaved biopsy sub-system is to provide the ability to inject high potency, anti-cancer drugs embedded in a viscous carrier, directly into a detected tumor if it is too large to use the hyperthermic technique described above. A further enhancement of the present system is to provide an endo-surgical system to deal with large detected cancers. The system uses a special needle to homogenize the tissue within the tumor and then aspirate the resulting debris. Once the cancer has been destroyed, the total removal of the malignant tissue is verified by the laser florescence technique (or by the use of the described bio-impedance system from within the created cavity, or alternatively by overlaying the ultrasonically mapped image of the cavity onto the stored image of the detected tumor mass.) Depending on the size of the created cavity, said cavity can be closed by creating a vacuum within the cavity to collapse it and then injecting a tissue adhesive to seal the cavity. Cavities that are too large for this technique are closed by filling them with a collagen gel that has been infused with the appropriate mixture of drugs. In order to absolutely preclude any "foreign body" reactions to the collagen gel, said collagen could be derived from the hair and fingernail clippings of that patient. Such a procedure produces a collagen gel that is completely biocompatible with that patient.

We claim:

1. A holistically integrated ultrasonic system for examining, mapping, diagnosing, and treating diseases of the prostate gland in a male human, the system comprising:

an ultrasonic transrectal probe and an ultrasonic transurethral probe, each of which is outfitted to pulse and to receive, and each of which is in operative communication with an integrated patient support platform;

the ultrasonic transrectal probe adapted to produce and operate within a liquid-filled volume of the rectum of the male human, and the ultrasonic transurethral probe adapted to produce and operate within a liquid-filled volume of the urethra of the male human;

the ultrasonic transrectal probe being adapted to remain in a fixed position after being inserted into the rectum of the male human, and the ultrasonic transrectal probe having ultrasonic sensors therein which are adapted for movement by a motor controlled by a computer, so that ultrasonic scans of the prostate gland are effected;

the ultrasonic transurethral probe being adapted to remain in a fixed position after being inserted into the urethra of the male human, and the ultrasonic transurethral probe having ultrasonic sensors therein which are adapted for movement by a motor controlled by a computer, so that ultrasonic scans of the prostate gland are effected;

the ultrasonic transrectal probe containing an integrated position sensor suite which provides angular and relational data to an integrated expert system;

an integrated expert system which collects data transmitted by sensors in the ultrasonic transrectal and the ultrasonic transurethral probes, utilizing analytical techniques and integrated results to produce level-of-suspicion mapping of the prostate gland with cancer probability assessments for areas contained within the level-of-suspicion mapping.

2. The system of claim 1, wherein the ultrasonic transrectal probe and the ultrasonic transurethral probe are adapted to produce and operate within aqueous liquid-filled volumes of the rectum of the male human and the urethra of the male human respectively.

3. The system of claim 1, wherein the ultrasonic transrectal probe is outfitted with a duct which provides a bleed off of air from the rectum of the male human, thereby allowing liquid to completely fill the volume of the rectum of the male human within which the ultrasonic transrectal probe is adapted to operate.

4. The system of claim 1, wherein the integrated patient support platform is in operative communication with a coacting automated slave biopsy subsystem the operation of which is controlled by position targeting data provided by functions of the ultrasonic transrectal probe and the integrated expert system, the automated slave biopsy subsystem being also adapted for specific area selection by a medical practitioner, as well as for achieving a redundancy-in-safety consideration.

5. The system of claim 4, wherein the integrated expert system comprises a software package containing predetermined distance and angle data for scan positions within the ultrasonic transrectal probe, together with mathematical equations, coupled with means employed in conjunction with ultrasonic data collection for deriving targeting coordinates for operation of the automated slave biopsy subsystem and direction of a biopsy needle to a selected point within the prostate gland.

6. The system of claim 5, wherein the biopsy needle is coupled with means for extracting a biopsy tissue sample from the prostate gland.

7. The system of claim 1, wherein the integrated patient support platform comprises a multi-degree of freedom positioning chair subsystem which is equipped with means for optimizing positioning of a patient for ultrasonic scanning procedures and recording an optimum position of the patient, thereby affording repeatability of ultrasonic scanning procedures for that patient.

8. The system of claim 1, wherein the integrated expert system includes a means for electronically storing complete data collection, mapping, and cancer probability assessments for each examination of a patient, coupled with means for automatically identifying changes in conditions between successive examinations of that patient.

9. The system of claim 1, which additionally comprises a catheter/catheter feeder operatively associated with the ultrasonic transurethral probe to facilitate effective utilization thereof, and a coacting articulated fiber optic scope to serve as a guide for optimal placement of the catheter within the urethra.

10. The system of claim 1, which additionally comprises dual ultrasonic sensors located within the ultrasonic transrectal probe to facilitate data collection and analysis, with application to shadow analysis, the dual ultrasonic sensors being selected from the group consisting of conventional transducers and phased arrays.

11. The system of claim 1, which additionally comprises pulse/echo means for evaluating tissue of the prostate gland, coacting with dynamic elastography means for evaluating induced vibration of tissue of the prostate gland, coacting with doppler means for measuring both induced dynamic vibration and blood flow for imaging and assessing vascular environment within the prostate gland, coupled with 4D doppler means for analyzing dynamic excitation of tissue of the prostate gland.

12. The system of claim 1, wherein the ultrasonic transrectal probe additionally comprises optical means for facilitating hand insertion, as well as mechanically supported introduction, of the ultrasonic transrectal probe into the rectum of the male human.

13. The system of claim 5, wherein the automated slave biopsy subsystem includes a modified biopsy needle, which is interchangeable with the biopsy needle, the modified biopsy needle being outfitted to include means for delivering thermal energy or a medication into the center of a small cancer of the prostate gland for eradication of the cancer.

14. The system of claim 5, wherein the automated slave biopsy subsystem includes a modified biopsy needle, which is interchangeable with the biopsy needle, the modified biopsy needle being outfitted to include means for introducing an eddy current into the center of a determined anomalous area of the prostate gland, in order to measure bioimpedance differential characteristics and thereby distinguish between a benign and a malignant anomalous area of the prostate gland.

15. The system of claim 6, wherein the biopsy needle has a symmetrical, wedge-shaped tip which is open on the forward aspect thereof and comprises integral side plates having conformal guides on inner faces thereof, which conformal guides force coacting dual square-ended cutting blades to follow curvature of the side plates and curve in behind a captive biopsy tissue sample to retain the captive biopsy tissue sample for subsequent extraction from the prostate gland.

16. The system of claim 5, wherein the automated slave biopsy subsystem is adapted to include means for automatically implanting radioactive seeds in the prostate gland in a brachytherapy procedure.

17. The system of claim 16, wherein the means for automatically implanting radioactive seeds in the prostate gland includes means for implanting radioactive seeds having a non-uniform radiation pattern to provide focusing and control over radiation deposition patterns, thereby preventing unwanted damage to viable tissue, coupled with means for providing rotational capability of the biopsy needle, thereby controlling the orientation of the radioactive seeds having a non-uniform radiation pattern.

18. The system of claim 5, wherein the automated slave biopsy subsystem includes means for removal of a cancer of the prostate gland in an endosurgical procedure.

19. The system of claim 5, additionally comprising means for providing verification of the targeting coordinates prior to direction of the biopsy needle to a selected point within the prostate gland.

20. The system of claim 1, wherein the ultrasonic transrectal probe and has a cover comprising: a first integral passageway containing means for providing liquid filling of a lumen into which the ultrasonic probe is to be inserted, in order to afford a continuous path for ultrasonic examination; and a second integral passageway containing means for inserting a fiber optic probe therein.

21. The system of claim 1, wherein high frequency ultrasound is employed as a modality for examining, mapping, diagnosing, and treating diseases of the prostate gland in a male human.

22. The system of claim 1, which employs a modality other than ultrasonics for examining, mapping, diagnosing, and treating diseases of the prostate gland in a male human.

* * * * *